US010467815B2

(12) United States Patent
Marom et al.

(10) Patent No.: US 10,467,815 B2
(45) Date of Patent: Nov. 5, 2019

(54) AUGMENTED REALITY PLANNING AND VIEWING OF DENTAL TREATMENT OUTCOMES

(71) Applicant: Align Technology, Inc., San Jose, CA (US)

(72) Inventors: Ozi Marom, Rishon LeZiyon (IL); Assaf Weiss, Yavne (IL); Maayan Moshe, Ra'anana (IL); Yingjie Li, Cary, NC (US); Phillip Thomas Harris, Cary, NC (US); Maurice K. Carrier, Durham, NC (US)

(73) Assignee: Align Technology, Inc., San Jose, CA (US)

( * ) Notice: Subject to any disclaimer, the term of this patent is extended or adjusted under 35 U.S.C. 154(b) by 0 days.

(21) Appl. No.: 15/841,212

(22) Filed: Dec. 13, 2017

(65) Prior Publication Data

US 2018/0174367 A1 Jun. 21, 2018

Related U.S. Application Data

(60) Provisional application No. 62/435,569, filed on Dec. 16, 2016, provisional application No. 62/568,220, filed on Oct. 4, 2017.

(51) Int. Cl.
*G06T 19/00* (2011.01)
*G06K 9/00* (2006.01)
(Continued)

(52) U.S. Cl.
CPC ............ *G06T 19/006* (2013.01); *A61B 34/10* (2016.02); *A61B 90/36* (2016.02); *A61C 7/002* (2013.01);
(Continued)

(58) Field of Classification Search
CPC .. G06K 9/00664–00704; G06F 3/0481; G06F 3/04817; G06F 9/4443;
(Continued)

(56) References Cited

U.S. PATENT DOCUMENTS 6,334,772 B1 1/2002 Taub et al.
6,334,853 B1 1/2002 Kopelman et al.
(Continued)

FOREIGN PATENT DOCUMENTS

KR 101678910 B1 12/2016
WO 2015/110859 A1 7/2015
(Continued)

OTHER PUBLICATIONS

Rozenfeld, M. "ModiFace Is Transforming the Beauty Industry With Augmented Reality," the institute, IEEE, Jul. 25, 2016, 4 pages.
(Continued)

*Primary Examiner* — Todd Buttram
(74) *Attorney, Agent, or Firm* — Lowenstein Sandler LLP

(57) ABSTRACT

A processing device generates a visual overlay comprising a virtual model of a dental arch that represents a treatment outcome for the dental arch. The processing device outputs the visual overlay to an augmented reality (AR) display or virtual reality (VR) display. The processing device receives user input based on a user interaction with the virtual model of the dental arch, wherein the user input modifies the virtual model of the dental arch and determines an update to the treatment outcome for the dental arch based on a user input. The processing device generates an updated treatment plan based on the update to the treatment outcome and updates the visual overlay, wherein the updated visual overlay comprises a view of the dental arch after the updated treatment outcome.

20 Claims, 15 Drawing Sheets

(51) Int. Cl.

| | |
|---|---|
| *A61C 7/00* | (2006.01) |
| *A61C 9/00* | (2006.01) |
| *G06F 3/01* | (2006.01) |
| *A61B 34/10* | (2016.01) |
| *A61B 90/00* | (2016.01) |
| *G02B 27/01* | (2006.01) |
| *G02B 27/00* | (2006.01) |
| *A61B 17/00* | (2006.01) |
| *A61B 90/50* | (2016.01) |
| *A61B 34/20* | (2016.01) |

(52) U.S. Cl.
CPC .......... *A61C 9/008* (2013.01); *G02B 27/0093* (2013.01); *G02B 27/017* (2013.01); *G06F 3/011* (2013.01); *G06K 9/00268* (2013.01); *A61B 2017/00216* (2013.01); *A61B 2034/105* (2016.02); *A61B 2034/2048* (2016.02); *A61B 2034/2065* (2016.02); *A61B 2090/365* (2016.02); *A61B 2090/3612* (2016.02); *A61B 2090/371* (2016.02); *A61B 2090/372* (2016.02); *A61B 2090/502* (2016.02); *G02B 2027/014* (2013.01); *G02B 2027/0138* (2013.01); *G02B 2027/0141* (2013.01); *G02B 2027/0178* (2013.01); *G02B 2027/0181* (2013.01)

(58) Field of Classification Search
CPC .. G06F 3/04847; G06F 11/3664; G06F 3/012; G06F 3/0304; G06F 3/011–015; G06T 19/00; G06T 17/00; G06T 19/006; G06T 2215/16; H04N 5/272; H04N 2201/3245; A63F 13/10

See application file for complete search history.

(56) References Cited

U.S. PATENT DOCUMENTS

| | | | |
|---|---|---|---|
| 7,249,952 B2 | 7/2007 | Ranta et al. | |
| 7,711,447 B2 | 5/2010 | Lu et al. | |
| 7,862,336 B2 | 1/2011 | Kopelman et al. | |
| 8,662,900 B2 | 3/2014 | Bell, III et al. | |
| 9,642,686 B1* | 5/2017 | Kalman | A61C 9/0053 |
| 2004/0091845 A1 | 5/2004 | Azerad et al. | |
| 2007/0197902 A1* | 8/2007 | Schutyser | G06T 7/0012 |
| | | | 600/416 |
| 2010/0015589 A1 | 1/2010 | Lehavi | |
| 2010/0145898 A1 | 6/2010 | Malfliet et al. | |
| 2013/0325431 A1* | 12/2013 | See | A61C 7/002 |
| | | | 703/11 |
| 2015/0025907 A1* | 1/2015 | Trosien | G06Q 10/10 |
| | | | 705/2 |
| 2015/0049081 A1* | 2/2015 | Coffey | G06T 19/006 |
| | | | 345/419 |
| 2015/0320320 A1 | 11/2015 | Kopelman et al. | |
| 2016/0220105 A1 | 8/2016 | Duret | |
| 2017/0065379 A1* | 3/2017 | Cowburn | A61C 19/04 |
| 2018/0168781 A1* | 6/2018 | Kopelman | A61C 1/0015 |
| 2018/0206940 A1* | 7/2018 | Kopelman | A61C 7/002 |

FOREIGN PATENT DOCUMENTS

| | | |
|---|---|---|
| WO | 2015/123759 A1 | 8/2015 |
| WO | 2016/200167 A1 | 12/2016 |
| WO | 2017/144934 A1 | 8/2017 |

OTHER PUBLICATIONS

'Invitation to Pay Additional Fees' and "Communication Relating to the Results of the Partial International Search" for International Application No. PCT/US2017/066849 dated Mar. 13, 2018, 14 pages.

\* cited by examiner

AUGMENTED REALITY PLANNING AND VIEWING OF DENTAL TREATMENT OUTCOMES

RELATED APPLICATIONS

This patent application claims the benefit under 35 U.S.C. § 119(e) of U.S. Provisional Application No. 62/435,569, filed Dec. 16, 2016, and further claims the benefit under 35 U.S.C. § 119(e) of U.S. Provisional Application No. 62/568,220, filed Oct. 4, 2017, both of which are incorporated by reference herein.

TECHNICAL FIELD

Embodiments of the present invention relate to the field of dentistry and, in particular, to a system and method for providing augmented reality enhancements for planning and viewing of dental outcomes.

BACKGROUND

Augmented reality devices may provide additional information to users of the devices in the context of the surrounding real world environment. For example, an augmented reality device may provide audio, video, graphic, or other information to a user to supplement the information available in the real world environment.

BRIEF DESCRIPTION OF THE DRAWINGS

Embodiments of the present invention are illustrated by way of example, and not by way of limitation, in the figures of the accompanying drawings.

DETAILED DESCRIPTION

Figure 1A:
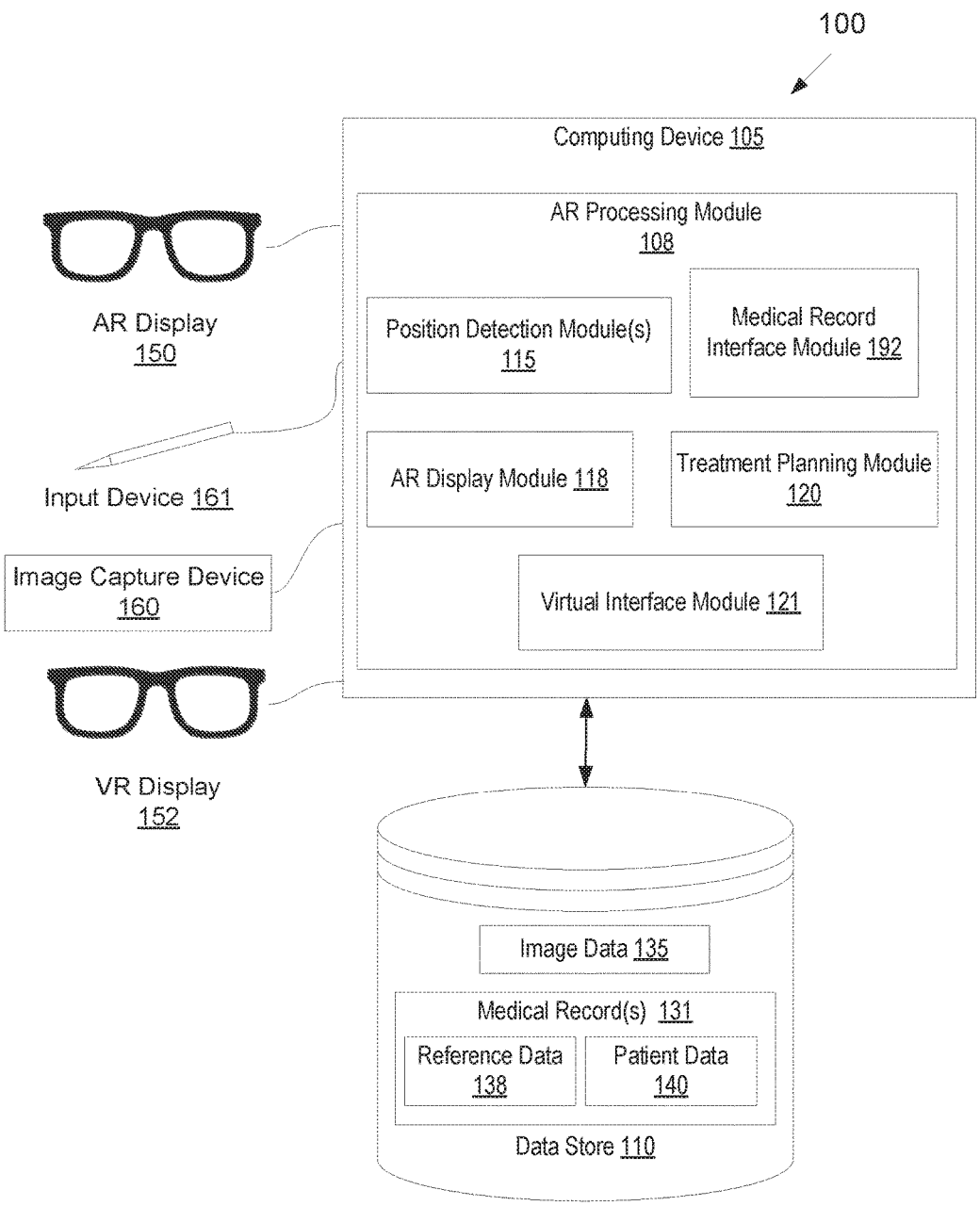
FIG. 1A illustrates one embodiment of an augmented reality system for enhancing the planning and viewing of treatment outcomes, in accordance with an embodiment.

Described herein are methods and apparatuses for providing augmented reality (AR) enhancements and virtual reality (VR) enhancements to the planning and viewing of dental outcomes as well as to the retrieval and editing of dental data. An AR system (also referred to herein as an AR device) may provide an overlay of a dental outcome on a mouth or dental arch of a subject as viewed through the AR display. The AR system or a VR system (also referred to herein as a VR device) may also provide an interface to plan a dental outcome and/or retrieve and view dental data. The interface may show alignment of a dental outcome on a subject's mouth or dental arch or may project a rendering of a two-dimensional (2D) or three-dimensional (3D) model to be manipulated through the interface. The interface may additionally show a rendering of other dental data, such as x-ray images, photographs, text, and so on.

To provide an overlay of a dental outcome on a subject, an image capture device associated with the AR system may capture images of the subject. The AR system may then process the image data to identify a mouth and a dental arch in the image data. In some embodiments, the AR system may also determine a position of the dental arch relative to the AR system. The AR system may then determine a treatment outcome for the subject. The treatment outcome may be determined based on analysis of the dental arch as received in the image data, based on a 3D model of the dental arch, based on x-ray or oral scanning information, or based on other data associated with the subject. The AR system may then generate a visual overlay comprising an indication of the treatment outcome. The AR system may determine a position for the visual overlay based on the position of the dental arch relative to the AR system, or an identified position of the dental arch in the image data. The visual overlay may then be outputted to an AR display such that it is superimposed over a view of the dental arch on the AR display. Accordingly, a dental practitioner wearing the AR display may see a patient as the patient will look after treatment outcome and/or a user wearing the AR display and looking into a mirror may see themselves as they would look after the treatment outcome.

After the AR system has determined a position of the dental arch and generated the visual overlay, the system may continue to track the position of the dental arch, a shape of the mouth, exposed portions of the mouth, movement of the lower jaw, or the like. Thus, the AR system can continue to update the visual overlay based on the tracked data to provide the treatment outcome superimposed on the dental arch of the subject. Accordingly, the treatment outcome may be provided in each frame of a live video feed.

An AR system providing a view of treatment outcomes include an AR display worn by a subject that is viewing himself in a mirror. For example, the AR system may include a pair of AR glasses. The image data generated by an imaging device of the AR display may include an image of the AR glasses as well as an image of the subject's mouth and dental arch. The AR system may use a position of the AR glasses in the mirror and a position of the subject's mouth in the mirror to coordinate a position of the subject's mouth as the AR glasses move. For instance, the AR system may track the position of the AR glasses based on movement in the received image data and/or based on accelerometers or other sensors that provide outputs that indicate a change in the position of the AR glasses.

In some embodiments, an AR system providing a view of treatment outcomes may include a display screen that shows a live feed of the subject and an overlay of the treatment outcome superimposed on the mouth of the subject. For example, the AR system may be a mobile device with a display screen, a kiosk acting as a smart mirror, or another AR system that has a display screen and cameras to capture image data including the subject. In some embodiments, an AR system may include AR glasses that are used by a dental practitioner or other individual to view the treatment outcome on a subject. For example, a dental practitioner may view the treatment outcome to ensure that the planned outcome will be aesthetically pleasing on the subject. In addition, the subject may have other persons view the subject with the treatment outcome in order to show what a final treatment outcome will look like.

In some embodiments, an AR system automatically retrieves dental data for a patient, and provides an interface for viewing and manipulating such dental data. In one embodiment, an AR system receives image data from an image capture device of the AR system. The AR system processes the image data to identify a patient identifier in the image data. The patient identifier may be, for example, a numerical code, a textual code, an alphanumeric code, a two-dimensional (2D) barcode, a 3D barcode, an image, or other type of patient identifier. Upon detection of the patient identifier in the image data, the AR system may use that patient identifier as a key to retrieve dental data from a medical record that is associated with the patient identifier. The AR system may then generate a rendering of the dental data (e.g., of a virtual 3D model of a dental arch of a patient) and output the rendering in an AR display of the AR system.

An AR system and/or VR system may also provide an interface for planning treatment outcomes. For example, based on a 3D model or oral scan information, a version of an idealized treatment outcome may be created. However, the idealized treatment outcome may not be the outcome preferred by a subject or a dental practitioner. In addition, an idealized treatment outcome may not take into account the position of the dental arch to a subject's face. For instance, the idealized treatment outcome may have a midline that is not the same as the midline of the subject's face. Accordingly, and AR system and/or VR system may provide an interface to improve treatment planning.

In some embodiments, the AR system may superimpose a treatment outcome on the mouth of a patient as discussed above. The AR system and/or VR system may also provide one or more indicators that provide information regarding the alignment of the treatment outcome with the alignment of the subject's face. For instance, a midline may be presented for both the treatment outcome and for the subject's face. If the midlines do not match, the AR system and/or VR system may enable the user to adjust the treatment outcome such that the midlines do match. The AR system and/or VR system may also provide an indication if the dental arch in the treatment outcome is too narrow or too wide for the subject's face. For example, if the subject has a wide smile, a narrow dental arch may not be preferred to a wider dental arch. Accordingly the AR system and/or VR system may provide an indicator of the difference and provide an interface to adjust the treatment outcome.

In some embodiments, an AR system and/or VR system may provide a treatment outcome planning interface without (or in addition to) projecting the treatment outcome on a subject. For example, a virtual two-dimensional (2D) or three-dimensional (3D) model of the dental arch may be projected on an AR display or VR display. A user may then interact with the virtual 2D or 3D model to make changes to a treatment outcome. In some embodiments, the AR system or VR system may have an associated haptic feedback device (e.g., a stylus, glove, or other instrument) that it can track with an electromagnetic sensor, proximity sensor, or the like, or track in imaging data from an imaging device. The movement of such an instrument may be used to move one or more teeth in the virtual 2D or 3D model of the dental arch.

The AR system and/or VR system may also provide feedback regarding possible changes to the treatment outcome. For example, a change to a treatment outcome that includes a change to a position of a tooth may not be possible if there is already another tooth in that position. The AR system and/or VR system may then provide feedback indicating that the change is not valid. The change may be indicated based on a visual indicator on the AR display or VR display or based on other feedback, such as haptic feedback through the instrument used to make the change. In some embodiments, different levels of feedback may be given based on the type of change. For instance, a first level of feedback may be given as a tooth is originally moved by the user, another may be given when the tooth being moved contacts another tooth, and another level of feedback may be given if the tooth is being moved into an invalid position. In various embodiments, other levels or types of feedback may be provided.

Embodiments provide significant advantages over traditional techniques for planning and viewing of dental outcomes. Dental practitioners can use an AR system as described herein to automatically retrieve dental data and/or other medical records for a patient. This enables a dental practitioner to easily access and view dental data without inputting a patient's name at a computer. Additionally, this enables a dental practitioner to view and/or modify dental data in a public setting without revealing any such private patient information to third parties. Dental practitioners can use an AR system and/or VR system as described herein to better interact with a patient's treatment plan or potential patient's treatment plan to plan and view dental outcomes. The AR system and/or VR system also presents information to a dental practitioner while the dental practitioner views a patient, and may reduce or eliminate a need for the dental practitioner to look away from the patient when planning treatment outcomes. In one embodiment, the AR system performs facial recognition when a patient's face enters a field of view (FOV) of an AR device. The facial recognition may be used to determine an associated medical record and automatically retrieve dental data from the medical record for a patient.

Furthermore, the AR system may be used by a patient or potential patient to view a treatment outcome. This may encourage the patient or potential patient to begin a treatment. Furthermore, the patient or potential patient may use the AR system to customize a treatment outcome. For example, a patient or potential patient may interact with their own treatment plan to have some control over the final treatment outcome. This may enable a patient who has a different aesthetic than standard to select how they want their teeth to look, such as by causing a slight gap between two or more teeth, and so on. Patients who are given some control over their treatment outcome may have increased treatment satisfaction. A dental practitioner may also use the AR system to change a treatment plan based on facial features, mouth shape, or other features of a subject. Embodiments therefore improve the efficiency of interfacing with patients, the quality of dental treatment outcomes, and enable additional customizations of treatment outcomes.

Embodiments described herein are discussed with reference to an AR system. An AR system is a device that enables a live direct or indirect view of a physical, real-world environment and that augments the view of the physical real-world environment by computer generated sensory input such as sound, video, or graphics. An AR system may include an AR display that includes glasses or other lenses that have one or more cameras attached to capture images of a patient. The AR display may also have a projector that projects images onto the glasses or lenses to provide a visual overlay to a dental practitioner. The visual overlay is superimposed over the real world image that the dental practitioner sees through the glasses or lenses. Some embodiments herein are described with reference to an AR display that is worn by a dental practitioner, such as AR glasses, AR goggles, or an AR headset. While some embodiments described herein are discussed with reference to a worn AR display, it should be understood that embodiments also apply to AR system that use other types of displays. For example, embodiments may apply to a computing device having a screen showing live images captured of a patient and overlay information to enhance the experience of the dental practitioner viewing the screen.

Additionally, it should be understood that embodiments described with reference to an AR system also apply to a virtual reality (VR) system. A VR system is similar to an AR system, except that an AR system allows a wearer or viewer to see an augmented version of the real world, while a VR system provides a purely simulated environment. A VR system artificially creates sensory experiences that can include sight, touch, sound, and/or other senses, and presents these sensory experiences onto a VR display. Any reference made herein to any type of AR system and/or AR display applies equally to a VR system and/or VR display.

FIG. 1A illustrates one embodiment of an AR system 100 for providing enhancements to the planning and viewing of dental outcomes. In one embodiment, the AR system 100 includes a computing device 105, an AR display 150, an image capture device 160, and a data store 110. In some embodiments, the components shown in FIG. 1A may be integrated into a device that houses the AR display 150. For example, the computing device 105 and image capture device 160 may be integrated into glasses or a headset to be worn by a dental practitioner or a patient. In some embodiments, the computing device 105 may be separate from the AR display 150, but connected through either a wired or wireless connection to a processing device in the AR display 150. Additionally, the data store 110 may be attached to the AR display 150, may be directly connected to computing device 105, and/or may be accessed by computing device 105 over a network (not shown). In some embodiments, the computing device 105 and data store 110 may be collocated and accessed by the AR display 150 over a network.

Computing device 105 may include a processing device, memory, secondary storage, one or more input devices (e.g., such as a keyboard, mouse, tablet, speakers, or the like), one or more output devices (e.g., a display, a printer, etc.), and/or other hardware components. Computing device 105 may be connected to data store 110 either directly or via a network. The network may be a local area network (LAN), a public wide area network (WAN) (e.g., the Internet), a private WAN (e.g., an intranet), or a combination thereof. The computing device 105 may be integrated into the AR display 150 or image capture device 160 in some embodiments to improve mobility.

Data store 110 may be an internal data store, or an external data store that is connected to computing device 105 directly or via a network. Examples of network data stores include a storage area network (SAN), a network attached storage (NAS), and a storage service provided by a cloud computing service provider. Data store 110 may include a file system, a database, or other data storage arrangement.

The AR display 150 may include lenses through which a wearer (e.g., a dental practitioner) may see a physical, real-world environment (e.g., a patient's oral cavity) and a projector for projecting visual elements onto the lenses. Examples of AR displays include Microsoft HoloLens®, Google Glass®, Vuzix Smart Glasses®, and Sony SmartEyeGlass®. The AR display 150 may therefore overlay information for a dental practitioner onto the lenses in a position in the field of view of the practitioner that corresponds to a location of an identified area of interest. To determine where to display information, the AR display 150 may include one or more sensors to track the eyes of a user and/or determine a position of the user in relation to positions of objects viewed by the user. The AR display 150 may also use images provided from image capture device 160 to determine where to display information to the dental practitioner. In some embodiments the image capture device 160 is mounted to the AR display 150.

As a dental practitioner wearing the AR display 150 views a patient, image capture device 160 may generate a stream of images that show the patient from the dental practitioner's point of view. Additionally, as a dental practitioner wearing the AR display 150 views a paper, screen (e.g., screen of a mobile phone, laptop computer, desktop computer, tablet computer, etc.) or other object that includes a patient identifier, the image capture device 160 may generate a stream of images that show the object from the dental practitioner's point of view. The image capture device may be or include a charge-coupled device (CCD) sensor and/or a complementary metal-oxide semiconductor (CMOS) sensor. The image capture device 160 may provide images or video to the computing device 105 for processing. For example, the image capture device 160 may provide images to the computing device 105 that the computing device analyzes to identify a patient's mouth, a patient's face, a patient's dental arch, a position of the AR device relative to the patient's arch or mouth, an object that includes a patient identifier, a position of the AR device relative to the object, or the like. The image capture device 160 may also provide images to the computing device 105 or AR display 150 that are used to coordinate the position of elements of a visual overlay to display on AR display 150 so that the visual overlay is superimposed over the real-world environment viewed by the dental practitioner or patient. In some embodiments, the images captured by image capture device 160 may be stored in data store 110. For example, the image data 135 may be stored in data store 110 as a record of patient history or for computing device 105 to use for analysis of the patient. The image capture device 160 may transmit the discrete images or video to the computing device 105. Computing device 105 may store the image data 135 in data store 110.

In some embodiments, the image capture device 160 provides two-dimensional data. In some embodiments, the image capture device 160 may provide three-dimensional data or stereoscopic image data that may be processed to produce three-dimensional data. For example, the image capture device 160 may have two cameras with a known separation and known imaging angles that simultaneously capture image data. The stereoscopic image data may be provided to computing device 105 as a single stream of image data or as two separate streams of image data. The stereoscopic image data may be used to provide an estimation of depth for objects viewed through the AR display 150. For example, the computing device 105 may use the stereoscopic image data to identify a three dimensional location of a tooth, mouth, dental arch, or other objects in the field of view of the image capture device 160.

The image capture device 160 may include high definition cameras to accurately capture the structure of areas of interest of a patient. In some embodiments, the image capture device 160 may have one or more cameras that capture a wide field of view and additional cameras for capturing a narrow field of view (e.g., for a region identified as a mouth or dental arch of a patient). In some embodiments, the image capture device 160 may include additional cameras to provide additional streams of image data. Additional cameras may be used to improve three dimensional image quality.

In some embodiments, the AR system 100 additionally or alternatively includes a virtual reality (VR) display 152 that may be worn by a patient or dental practitioner. The image data from the image capture device 160 and/or the visual overlay generated based on the image data may be output to the VR display 152. This may enable the patient or dental practitioner to view treatment outcomes that a dental practitioner is seeing and potentially updating. This may facilitate an explanation of the treatment outcome and provide an opportunity for the patient to have input into a treatment plan. Image data from the image capture device and/or visual overlays may be synchronized between an ARNR device of a dental practitioner and an AR/VR device of the patient such that the patient and dental practitioner may discuss and generate a treatment plan together based on the combined AR/VR experience.

In some instances the image capture device 160 may be separate from the VR display 152 and AR display 150, and may be directed toward a wearer of the AR display 150 and/or VR display 152. The image capture device 160 may project structured light (e.g., a grid of lines and/or dots) to assist in obtaining 3D image data. The image capture device 160 may capture image data of an object such as an input device 161 (e.g., which may be a haptic device), a user hand, and so on. This image data may be used to determine a position of the input device 161 relative to a virtual model (e.g., a virtual 3D model of a dental arch) that is projected onto the AR display 150 and/or VR display 152. In some embodiments, the object is an object that includes a patient identifier. The computing device 105 may identify the patient identifier in the object, and may determine an orientation and/or position of the object and/or of the patient identifier on the object. The orientation and/or position of the object (or of the patient identifier on the object) may be used to determine where to project a rendering of dental data such as a virtual 3D model of a dental arch.

Input device 161 may be a haptic device such as haptics gloves, a stylus, a pointer or other instrument that includes haptics components capable of providing forces, vibrations and/or motions for haptic feedback. The input device 161 may include one or more sensors such as a gyroscope, accelerometer, etc. capable of detecting changes in position of the haptic device. Additionally, or alternatively, the AR system 100 may include one or more additional external sensors (not shown) that interface with the input device 161 to accurately determine a position and orientation of the input device 161. The relative position of the input device 161 and a virtual model of a dental arch may then be determined, and the input device 161 may interact with and adjust the virtual model of the dental arch.

In one embodiment, the input device 161 is any device that includes a patient identifier. Examples of such devices include a paper that includes a printout of the patient identifier, a mobile phone, tablet computer, laptop computer, desktop computer, etc. with a screen image showing the patient identifier, and so on. The input device 161 may also be a device that includes an input device identifier. An input device identifier may be a numerical code, a textual code, an alphanumeric code, a 2D barcode, a 3D barcode, an image, etc. that is associated with an input device. The input device identifier may be used to identify an object that is in a field of view (FOV) of the AR display 150 as an input device. Alternatively, or additionally, computing device 105 may include a record of the known geometry of an input device. If an object having the known geometry is detected in the FOV of the AR display 150, that object may be identified as an input device. Examples of input devices that may include input device IDs or have a known shape include a pointer, a pen, a cube, a wand, a paper, a block, or any other type of object that can fit in a hand.

The computing device 105 may include AR processing module 108. The AR processing module 108 may analyze image data 135 from a data store 110 or directly from an image capture device 160. The AR processing module 108 may then identify a mouth, a dental arch, an AR device, a patient identifier, an input device, or other objects and/or information in the image data. The AR processing module 108 may then generate on or more visual overlays to output to AR display 150 and/or generate additional information to present on the AR display 150. The information provided on an AR display 150 may depend on a wearer of the AR display 150, data in medical records 131 (e.g., information known about a patient (patient data 140 such as dental data and/or a treatment outcome), or the like. For example, if a patient, prospective patient, or dental practitioner is using the AR device, the computing device 105 may provide an overlay of a treatment outcome to the patient. The AR device may also or alternatively provide an interface enabling a patient, prospective patient, or dental practitioner to design or modify a treatment outcome displayed on an AR display 150 or VR display 152.

By way of non-limiting example, a treatment outcome may be the result of a variety of dental procedures. Such dental procedures may be broadly divided into prosthodontic (restorative) and orthodontic procedures, and then further subdivided into specific forms of these procedures. Additionally, dental procedures may include identification and treatment of gum disease, sleep apnea, and intraoral conditions. The term prosthodontic procedure refers, inter alia, to any procedure involving the oral cavity and directed to the design, manufacture or installation of a dental prosthesis at a dental site within the oral cavity, or a real or virtual model thereof, or directed to the design and preparation of the dental site to receive such a prosthesis. A prosthesis may include any restoration such as implants, crowns, veneers, inlays, onlays, and bridges, for example, and any other artificial partial or complete denture. The term orthodontic procedure refers, inter alia, to any procedure involving the oral cavity and directed to the design, manufacture or installation of orthodontic elements at a dental site within the oral cavity, or a real or virtual model thereof, or directed to the design and preparation of the dental site to receive such orthodontic elements. These elements may be appliances including but not limited to brackets and wires, retainers, clear aligners, or functional appliances. Any of treatment outcomes or updates to treatment outcomes described herein may be based on these orthodontic and/or dental procedures. Examples of orthodontic treatments are treatments that reposition the teeth, treatments such as mandibular advancement that manipulate the lower jaw, treatments such as palatal expansion that widen the upper and/or lower palate, and so on. For example, an update to a treatment outcome may be generated by interaction with a user to perform one or more procedures to one or more portions of a patient's dental arch or mouth. Planning these orthodontic procedures and/or dental procedures may be facilitated by the AR system described herein.

A treatment plan for producing a particular treatment outcome may be generated by first generating an intraoral scan of a patient's oral cavity. From the intraoral scan a virtual 3D model of the upper and/or lower dental arches of the patient may be generated. A dental practitioner may then determine a desired final position and orientation for the patient's teeth on the upper and lower dental arches, for the patient's bite, and so on. This information may be used to generate a virtual 3D model of the patient's upper and/or lower arches after orthodontic treatment. This data may be used to create an orthodontic treatment plan. The orthodontic treatment plan may include a sequence of orthodontic treatment stages. Each orthodontic treatment stage may adjust the patient's dentition by a prescribed amount, and may be associated with a 3D model of the patient's dental arch that shows the patient's dentition at that treatment stage.

In one embodiment, AR processing module 108 includes one or more position detection modules 115, an AR display module 118, a treatment planning module 120, a medical record interface module 192 and a virtual interface module 121. Alternatively, the operations of one or more of the position detection modules 115, AR display module 118, medical record interface module 192, virtual interface module 121 and/or treatment planning module 120 may be combined into a single module and/or divided into multiple modules.

Position detection modules 115 are responsible for identifying a position of a mouth, a dental arch, and/or an AR device from image data 135 received from image capture device 160. The image data may be images of a patient's face and oral cavity viewed by a dental practitioner or patient wearing the AR display 150. The position detection modules 115 may, in identifying the position of a dental arch, analyze image data 135. The analysis may involve direct analysis (e.g., pixel-based and/or other point-based analysis), the application of machine learning, the application of image registration, and/or the application of image recognition. The position detection modules 115 may identify such positions directly from the image data 135 received from the image capture device 160 or based on a comparison of the received image data 135 and reference data 138 or previous patient data 140. For example, a position detection module 115 may use one or more algorithms to identify the shape of a tooth, the color of a tooth, the position of a tooth, the shape, color, or position of a mouth, or other characteristics of a tooth, mouth, or face to determine a position of a mouth for overlaying a treatment outcome for viewing by a dental practitioner or patient.

AR display module 118 is responsible for determining how to present the treatment outcome, dental data, or an interface for updating a treatment outcome on the AR display 150. AR display module 118 may provide an overlay of the treatment outcome on the AR display 150. The AR display module 118 may determine a position to project a virtual object in a visual overlay on an AR display 150 such that the visual overlay is positioned in the line of sight of the dental practitioner over the patient's oral cavity. The virtual object may include an overlay of the treatment outcome that may also include text, numbers, a contour, colors, graphical images and/or other virtual objects. For instance, the AR display module 118 may determine a position to display the treatment outcome based on the image data 135 and a corresponding position to project that treatment outcome on the AR display 150. In some embodiments, the AR display 150 may provide additional indicators separate from the treatment outcome in order to provide additional data to a dental practitioner and/or patient. For example, the AR display 150 may display an indication of midlines, facial features, or other elements that aid in the generation of a treatment plan for a patient.

The AR display module 118 may provide the indications in the form of flags, markings, contours, text, images, and/or sounds (e.g., in the form of speech). In some embodiments, the AR display module 118 may provide one or more midlines so as to indicate the midline of the patient's dental arch and/or face in the image data 135. In some embodiments, the wearer of the AR display 150 may provide an indication of an identity of the wearer (e.g., through a menu or other user interface). AR processing module 108 may then determine what information to include in the visual overlay based on the identity of the wearer. For example, first information may be shown to a dentist and second information may be shown to a patient. In some instances, the AR processing module 108 provides a number of potential or recommended updates to a treatment plan for the patient or practitioner. Such updates may show up as a visual overlay on the AR display 150.

In some embodiments, a treatment planning module 120 is responsible for determining what data to present on AR display 150 based on potential updates to a treatment plan for a patient. In some embodiments, the treatment planning module 120 may also receive input or provide output to one or more instruments used for planning a treatment outcome for a patient. The treatment planning module 120 may access patient data 140, image data 135, and reference data 138 to determine AR elements to provide on AR display 150. In some embodiments, the treatment planning module 120 may receive or generate one or more virtual 3D models, virtual 2D models, or other treatment outcome models based on the reference data 138, patient data 140, or image data 135 received from an image capture device 160. For example, an intraoral scan of the patient's oral cavity may be performed to generate an initial virtual 3D model of the upper and/or lower dental arches of the patient. Treatment planning module 120 may then determine a final treatment outcome based on the initial virtual 3D model, and then generate a new virtual 3D model representing the final treatment outcome.

In one embodiment, virtual interface module 121 identifies an object in image data that represents an input device. Virtual interface module 121 may identify the object as an input device based on a geometry of the object, based on the object including a patient identifier and/or based on the object including an input device identifier. The virtual interface module 121 may map the position and orientation of such an input device (object) to the position and orientation of dental data such as a virtual 3D model. If the position or orientation of the input device changes, then the position and/or orientation of the dental data may likewise change. The virtual interface module 121 may also provide tracking of instruments in the view of image data 135 received from image capture device 160 to determine a user input to update a treatment outcome for the patient. For example, the treatment planning module may receive a position of the input device 161 or another AR interactive instrument from position detection module 115 that indicates a position and/or interaction from the input device 161 or other AR interactive instrument. The interaction may be used to update the virtual 3D or virtual 2D model, that the adjustment to the virtual 3D or virtual 2D model may be used to update the treatment plan for a patient.

In one embodiment, AR processing module 108 includes a medical record interface module 192. Medical record interface module 192 may search image data received from AR display 150 for a patient identifier. Once a patient identifier is determined, medical record interface module 192 may use that patient identifier to retrieve patient data 140 (e.g., dental data) from data store 110. In one embodiment, medical record interface module 192 uses an application programming interface (API) such as a Rest API or other communications protocol to establish two way communication between the AR system and one or more data stores 110 for retrieving dental data and/or storing updates to dental data. Each medical record 131 may be associated with a particular patient identifier, which may be used as a key to retrieve the patient data 140 associated with the medical record 131.

Figure 1B:
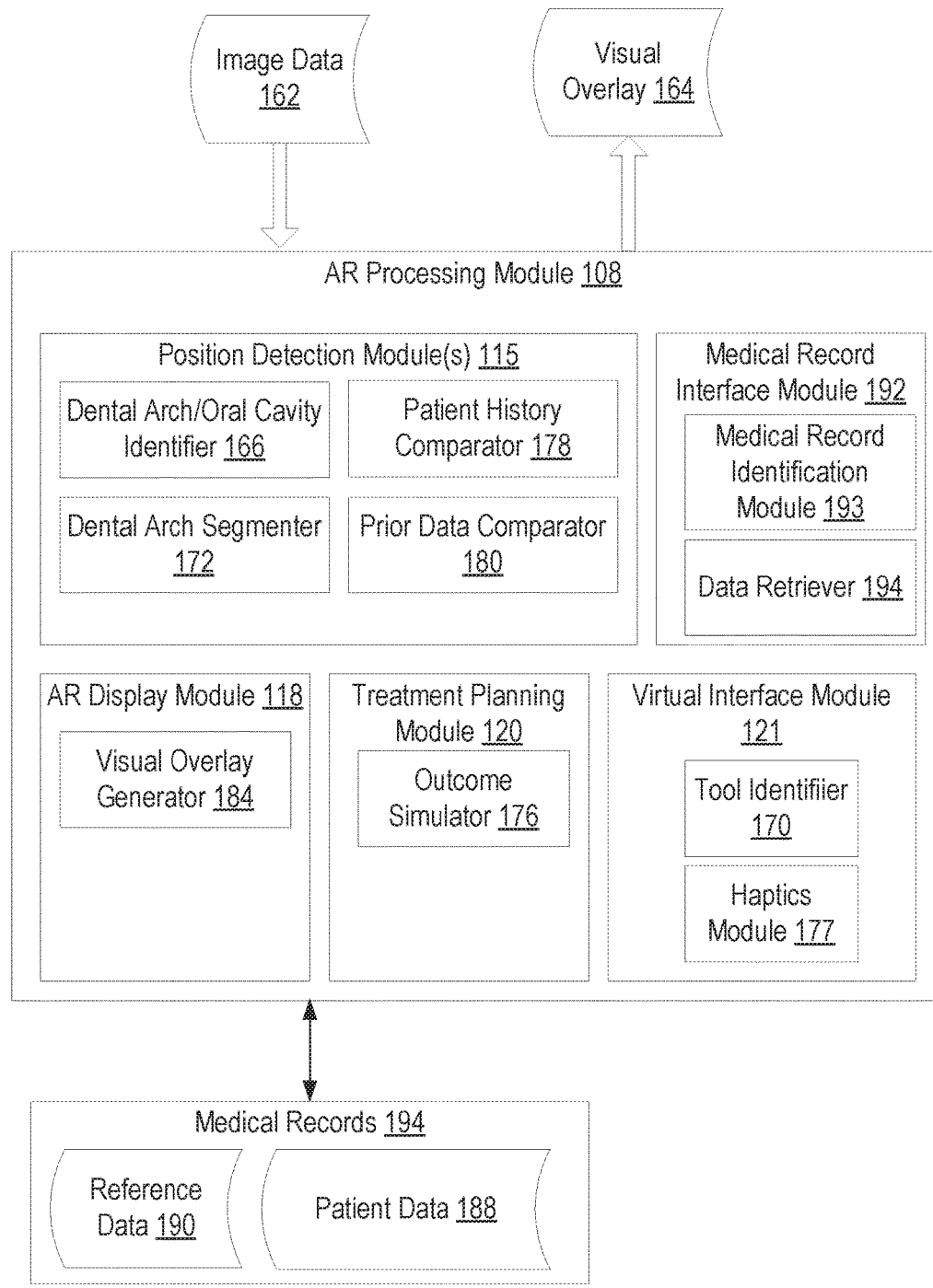
FIG. 1B illustrates one embodiment of an augmented reality processing module, in accordance with an embodiment.

FIG. 1B illustrates one embodiment of an augmented reality processing module 108, in accordance with an embodiment. The AR processing module 108 may correspond to AR processing module 108 of FIG. 1A in embodiments. AR processing module 108 may receive as an input image data 162 from image capture device 160, process the image data 162, and generate a visual overlay 164 that is then output to the AR display 150. The image data 162 may include an image of a patient's oral cavity that includes a dental arch (or two dental arches). The image data 162 may alternatively or additionally include an image of an object that includes a patient identifier and/or an object that includes an input device identifier.

AR processing module 108 may process the image data 162 to determine a position of a patient's mouth, a dental arch, an input device, a patient identifier, the AR display, a position of the dental arch relative to the AR display, or the like. The AR processing module 108 may generate the visual overlay 164 based on a treatment outcome for the position of the patient's mouth, dental arch, and the AR display. The AR processing module 108 may also generate the visual overlay 164 based on the patient data 188 (e.g., dental data) retrieved from a medical record 194 and/or based on a position and/or orientation of an input device. Notably, the image data 162 may represent a real-world scene as viewed by a dental practitioner or patient wearing an AR display. AR processing module 108 may receive the image data 162, process the image data, and output the visual overlay 164 to the AR display in real time or near-real time so that the visual overlay corresponds to the scene that the dental practitioner or patient is currently viewing through the AR display. The AR processing module 108 may receive a stream of image data 162 from the image capture device 160 and may output a stream of the visual overlay 164 that corresponds to the incoming stream of image data 162. Thus the visual overlay 164 may be continually updated in real time or near-real time to maintain correspondence to the scene as viewed by the dental practitioner as a patient moves, the dental practitioner moves, or the scene otherwise changes.

In embodiments in which the AR processing module is a VR processing module for a VR system, the incoming image data 162 may not represent a view of a wearer of the VR display. Instead, the image data 162 may represent a position of a wearer of the VR display and/or a position of a haptics device or other AR or VR interactive device such as a pointer, wand, gloves, and so on. Additionally or alternatively, other position data may also be received, which may include accelerometer data of the haptics device, gyroscope data of the haptics device, radio frequency time of flight data of the haptics device, and so on. This additional position data and/or the image data 162 may be used to accurately determine a position of the haptics device so as to determine any interaction between the haptics device and elements of the visual overlay 164, such as elements of a virtual 3D model of a patient's dental arch.

In one embodiment, AR processing module 108 includes multiple position detection modules 115. For instance, individual position detection modules 115 may detect the position of different components of a patient's face. Alternatively, one or more of these position detection modules 115 may be combined into a single position detection module 115. Each position detection module 115 is configured to detect the position of particular types of objects from the image data and/or track individual objects in the image data. In some embodiments, different position detection modules 115 may identify different objects in the image data using a variety of techniques. In some embodiments, the AR processing module 108 may include a dental arch/oral cavity identifier 166, a dental arch segmenter 172, a patient history comparator 178, a prior image data comparator 180, or other modules to detect objects and determine a position of those objects in received image data.

Dental arch/oral cavity identifier 166 may be responsible for identifying an oral cavity in received image data 162 and for identifying a dental arch in the oral cavity. To identify the oral cavity, dental arch/oral cavity identifier 166 performs image processing on the image data 162 using image recognition techniques. For example, oral cavities have visual cues that can be used to pinpoint the oral cavities in the image data 162. Dental arch/oral cavity identifier 166 may include an oral cavity profile that may have been generated using machine learning techniques such as neural networks. Processing the image data 162 may include first pre-processing the image data such as by performing re-sampling in a new coordinate system, performing noise reduction, enhancing contrast, adjusting scale, etc. Processing the image data 162 may additionally include performing feature extraction to identify lines, edges, ridges, point clouds, corners, point blobs, and so on. Processing the image data 162 may additionally include performing detection and/or segmentation to select those lines, edges, ridges, point clouds, corners, point blobs, etc. that represent the oral cavity and/or objects within the oral cavity.

Dental arch/oral cavity identifier 166 can identify the dental arch (or multiple dental arches) in the oral cavity using similar techniques as described for identifying the oral cavity. However, a dental arch profile may be used to identify the dental arch.

In an example, dental arch/oral cavity identifier 166 may identify features in the image data based on geometric analysis of the image data 162. The dental arch/oral cavity identifier 166 may perform geometric analysis based on identification of lines or color blobs in the image data 162. The geometric analysis may identify the features of an oral cavity and/or the features of a dental arch.

The dental arch/oral cavity identifier 166 may then determine a position of identified dental arches or oral cavities. For example, the dental arch/oral cavity identifier 166 may identify the dental arch or oral cavity based on stereoscopic imaging data and determine a position of the identified dental arch or oral cavity in a 3D space relative to the AR display. In some embodiments, a patient may be viewing a mirror, and the imaging data may include images of the mirror with the patient and AR display present in the imaging data. The dental arch/oral cavity identifier 166 may then determine a position of the dental arch or oral cavity in the imaging data, relative to the AR display based on the image in the mirror, or both.

In some embodiments, the dental arch/oral cavity identifier 166 may also determine a position of the AR display in the image data 162. For example, if a patient is looking in a mirror through AR glasses, the image data 162 may include an image of the AR glasses. Accordingly, the AR processing module 108 may determine a position of the AR glasses in the image data 162. The AR processing module 108 may then determine a position of the oral cavity or dental arch relative to the AR glasses. When tracking the position of the oral cavity or dental arch, the AR processing module 108 may then use information about the position of the AR glasses. For example, the AR glasses may provide an output that indicates a change in the position of the AR glasses based on a motion sensor. The AR processing module 108 may then estimate a position of the dental arch based on the change of the position of the AR glasses. For example, in some embodiments, the dental arch/oral cavity identifier 166 may determine an offset vector between the AR glasses and the upper jaw of a patient. While the AR glasses are worn by the patient, the distance between the AR glasses and the upper arch may remain fixed. The dental arch/oral cavity identifier 166 may then receive an indication that the AR glasses moved. In response to a new position indicated by the movement of the AR glasses, the AR processing module 108 may determine a new position of the upper jaw of the patient by applying the offset vector to the new position of the AR glasses.

Dental arch segmenter 172 may be responsible for segmenting an identified dental arch into individual teeth. The dental arch segmenter 172 may operate on similar principles as the dental arch/oral cavity identifier. Dental arch segmenter 172 may receive a subset of image data 162 that has already been processed by dental arch/oral cavity identifier 166 (e.g., point blobs, contours, ridges, corners, point clouds, etc. that represent a dental arch), and may perform detection and segmentation to segment the dental arch into the individual teeth. Dental arch segmenter 172 and/or dental arch/oral cavity identifier 166 may additionally identify gums in the oral cavity represented in the image data 162 and separate the gums from the teeth. The dental arch segmenter 172 may provide the information to an AR display module 118 to use when generating an overlay of a patient's treatment outcome or a treatment planning module 120 that may use the information to enable a user to interact with individual teeth to modify a treatment outcome.

In some embodiments a patient may wear markers on one or more teeth. These markers may be used by dental arch segmenter 172 to identify and segment individual teeth. Additionally, these markers may be used by dental arch/oral cavity identifier 166 to facilitate locating the oral cavity and dental arch in the image data 162. The markers may be stickers or other adhesives with known shapes or patterns that are easily identifiable in the image data 162.

In some embodiments, the position detection module 115 may apply algorithms that compare image data or features detected in image data to reference data 190, which may include a store of dental arch or oral cavity models or images. In some embodiments, the position detection module 115 may extract a model, image, set of edges, a point blob, set of contours, and/or other representation of a feature detected in the image data 162. The position detection module 115 may then compare the extracted model, set of edges, point blob, set of contours, image or other representation of the feature to the reference data 190 to identify a dental arch or oral cavity in the image data. The position detection module 115 may then determine a position of the dental arch or oral cavity.

In some embodiments, the position detection modules 115 additionally include a prior data comparator 180. The prior data comparator 180 may identify or help identify a dental arch or oral cavity by comparing image data 162 to prior image data included in previous patient data 188. Patient data 188 may include past data regarding the patient (e.g., medical records), previous or current scanned images or models of the patient, current or past X-rays, 2D intraoral images, 3D intraoral images, virtual 2D models, virtual 3D models, or the like.

Prior data comparator 180 may perform image registration between the image data 162 and the prior image data of a patient's oral cavity, dental arch, individual teeth, or other intraoral regions. Image registration algorithms are carried out to register the current image data 162 from the image capture device of the AR system to one or more previous mages of a patient's mouth, dental arch, teeth, etc. The image registration involves determination of the transformations which align one image with the other. Image registration may involve identifying multiple points, point clouds, edges, corners, etc. in each image of an image pair, surface fitting to the points of each image, and using local searches around points to match points of the two images. For example, prior data comparator 180 may match points of one image with the closest points interpolated on the surface of the other image, and iteratively minimize the distance between matched points. Prior data comparator 180 may also find the best match of curvature features at points of one image with curvature features at points interpolated on the surface of the other image, with or without iteration. Prior data comparator 180 may also find the best match of spin-image point features at points of one image with spin-image point features at points interpolated on the surface of the other image, with or without iteration. Other techniques that may be used for image registration include those based on determining point-to-point correspondences using other features and minimization of point-to-surface distances, for example. Other image registration techniques may also be used.

Many image registration algorithms perform the fitting of a surface to the points in adjacent images, which can be done in numerous ways. Parametric surfaces such as Bezier and B-Spline surfaces are common, although others may be used. A single surface patch may be fit to all points of an image, or alternatively, separate surface patches may be fit to any number of a subset of points of the image. Separate surface patches may be fit to have common boundaries or they may be lit to overlap. Surfaces or surface patches may be fit to interpolate multiple points by using a control-point net having the same number of points as a grid of points being fit, or the surface may approximate the points by using a control-point net which has fewer number of control points than the grid of points being fit. Various matching techniques may also be employed by the image registration algorithms.

In one embodiment, prior data comparator 180 may determine a point match between images, which may take the form of a two dimensional (2D) curvature array. A local search for a matching point feature in a corresponding surface patch of another image is carried out by computing features at points sampled in a region surrounding the parametrically similar point. Once corresponding point sets are determined between surface patches of the two images, determination of the transformation between the two sets of corresponding points in two coordinate frames can be solved. Essentially, an image registration algorithm may compute a transformation between two images that will minimize the distances between points on one surface, and the closest points to them found in the interpolated region on the other image surface can be used as a reference. The transformation may include rotations and/or translational movement in up to six degrees of freedom (e.g., rotations about one to three axes and translations within one to three planes). Additionally, the transformation may include changes in image size (e.g., zooming in or out) for one or both of the images. A result of the image registration may be a transformation matrix that indicates the rotations, translations and/or size changes that will cause the one image to correspond to the other image. In one embodiment, the transformation matrix is applied to the prior image data to cause the prior image data to correlate with the current image data 162.

In some instances, the previous image data to which the current image data 162 is registered comprises a three dimensional model of a patient's dental arch and/or jaw. The three dimensional model may have been generated at a previous time based on an intraoral scan of the patient's upper and/or lower dental arches. The three dimensional model may include the upper and lower dental arches, and may reflect articulation of a patient's jaw and tooth contact points between the upper and lower dental arch. To register the image data 162 to the three dimensional model, prior data comparator 180 may digitally construct multiple images of the three dimensional model from different perspectives. If the image data is two-dimensional image data, then each of the digitally constructed images may be two-dimensional images. Prior data comparator 180 may then attempt to register each of the digitally constructed images to the current image data 162 until registration is successful for one of the digitally constructed images. The perspective used to generate the registered digitally constructed image to the image data 162 is known, and so the three dimensional model may be registered to the image data 162.

Once the prior image data has been registered to the current image data 162 and transformed to match the current image data 162 as closely as possible, the transformed previous image data (or a portion thereof) may be used to generate visual overlay 164. For instance, the image registration may be used by the dental arch/oral cavity identifier 166 to determine a position of a dental arch, oral cavity, or other feature based on the alignment of the image data 162 to the previous patient data 188. Accordingly, a patient's historical dentition as represented in the previous image data may be adjusted to a current view point of a dental practitioner wearing an AR display. The AR device may then generate a visual overlay showing a treatment outcome superimposed over the current view of the AR display.

AR display module 118 is responsible for determining how to present a treatment outcome on the AR display 150. In one embodiment, AR display module 118 includes a visual overlay generator 184 that is responsible for generating the visual overlay 164 that may be superimposed over a real-world scene viewed by a dental practitioner or patient. Alternatively, AR display module 118 may generate a visual overlay 164 that is the only scene viewed by a wearer of a VR display. The visual overlay may be, for example, a virtual 3D model of a dental arch that appears to float in front of a wearer of the VR display.

In the case where the AR display module 118 is creating a visual overlay 164 for sending to an AR display (rather than to a VR display), the visual overlay generator 184 may determine a position to project the visual overlay 164 on the AR display 150 such that the visual overlay is positioned in the line of sight of the dental practitioner or patient over the dental arch of the patient in the real-world scene viewed by the dental practitioner or patient. For instance, the visual overlay generator 184 may determine from the position of the oral cavity or dental arch in the image data 162 a corresponding position to project a final treatment outcome of the dental arch on the AR display 150. In some embodiments, the AR system is a kiosk, mobile device, or other device with a display screen that captures image data of a patient and provides a video feed of the patient on a display. The visual overlay generator 184 may generate an overlay to modify the image data 162 to include a treatment outcome for the patient.

In some embodiments, a treatment planning module 120 is responsible for providing an interface for a dental practitioner or a patient to generate or modify a treatment outcome and a treatment plan for a patient. The interface may either be provided as part of an overlay on a patient's oral cavity or dental arch or as a virtual 2D or 3D model of a dental arch representing the patient's treatment outcome. The virtual 2D or 3D model of the dental arch may be shown separate from or together with an image of the patient's face.

In some embodiments the treatment planning module 120 may provide data to the AR display module 118 to generate an overlay of a generated treatment outcome on a patient's face. The treatment planning module 120 may then identify one or more features in the patient's face or the treatment outcome and provide an indication of those features. For example, the treatment planning module 120 may provide an indication of the midline of a current dental arch, the dental arch in a treatment outcome, the patient's face, or a combination of midlines. The treatment planning module 120 may also provide an indication that a treatment outcome may be too narrow or too wide based on the overlay with the patient's face.

In some embodiments, the treatment planning module 120 may provide a virtual 2D or 3D model of a patient's dental arch to the AR display module 118 to provide a visual overlay of the patient's dental arch. For instance, a visual overlay may include an enlarged version of the virtual 2D or 3D model of a patient's dental arch. The virtual 2D or 3D model of the dental arch may then be manipulated by the patient or the dental practitioner to update a treatment outcome. For instance, a patient may customize a dental arch to include a small gap in the midline or introduce another feature that an idealized treatment outcome may not include, but that the patient finds desirable.

In order to plan a treatment outcome, the treatment planning module 120 may include an outcome simulator 176. The outcome simulator 176 may take image data 162, previous patient data 188 (e.g., a 3D model of the patient's dental arch), reference data 190, and/or other data and generate a treatment outcome for the patient's dentition. The outcome simulator 176 may generate an idealized version of the patient's dentition based on algorithms that position the teeth to proper curvature and position relative to one another.

In some embodiments, the outcome simulator 176 may also provide information on treatment outcomes that are modified by a patient or dental practitioner. The outcome simulator 176 may have a set of rules that describe valid and invalid positions of various teeth. For instance, rules may determine invalid curvatures of a dental arch, teeth that overlap, teeth that are too close together, teeth that are too far apart, or the like. The outcome simulator 176 may update a treatment outcome based on input from a dental practitioner or a patient. The outcome simulator 176 may then determine whether such a treatment outcome is valid or may need to be changed further before it is decided upon as a final treatment outcome for the patient's treatment.

In some embodiments, the outcome simulator 176 may provide additional information regarding cephalometric analysis of a patient. The outcome simulator 176 may determine one or more cephalometric characteristics based on received image data 162 or intraoral scan or x-ray data in previous patient data 186. The x-ray data may include a cone beam tomography (CBCT) image, a panoramic x-ray image, one or more traditional x-ray images, and the like. The cephalometric characteristics may include one or more distances or angles describing the position of features of the patient's face relative to each other. In some embodiments, the outcome simulator 176 may estimate changes to the cephalometric characteristics based on a treatment outcome for the patient. If the treatment outcome is updated by the patient or dental practitioner, the cephalometric analysis may be updated accordingly. Thus, as the treatment outcome is updated, the cephalometric characteristics may also be updated. The treatment planning module 120 may provide the cephalometric analysis to the AR display module 118 to provide as a visual overlay. For instance, alignment indicators, distance indicators, or angle indicators may be provided as part of a visual overlay that shows characteristics of a patient's face. In some embodiments, if the cephalometric analysis is based on intraoral scan or x-ray data, the scan or x-ray data may be superimposed as a visual overlay on the patient's face in addition or alternative to particular cephalometric characteristics.

In some embodiments, virtual interface module 121 is responsible for enabling a user (e.g., a dental practitioner) to interface with dental data such as a virtual 3D model of a dental arch from medical records 194. In some embodiments, the virtual interface module 121 is a component of treatment planning module 120. Virtual interface module 121 may have a tool identifier 170 that identifies and tracks the position of one or more tools or instruments used by a dental practitioner or a patient. In some embodiments, a tool may be identified based on the image data 162. For instance, if a user is holding a haptic feedback device, stylus or other object that is captured in the image data 162, the tool identifier may identify the device and determine a position of the device. The tool identifier 170 may identify an input device based on the input device having a detectable patient identifier, a detectable input device identifier, or a detectable geometric configuration. The input device may be mapped to a rendering of a virtual 3D model of a dental arch so that any change in the position and/or orientation of the input device causes a corresponding position and/or orientation of a rendering of the virtual 3D model in a visual overlay.

Additionally, for some input devices (tools), the position of the device and any signals received from the device may be used to update a treatment outcome based on interactions by the user. In some embodiments, tools include sensors that may be used to facilitate tracking by the tool identifier 170. This may increase an accuracy of tracking the tools verses relying solely on tracking of the tools from the image data 162. For example, dental tools may include accelerometers, gyroscopes, magnetic tracking sensors, or the like. A position of the image capture device on the tool, a field of view of the image capture device, etc. may be known, and a relative position of the image capture device to a tool tip (or other interactive portion of a tool) may be known. Accordingly, captured images may be registered to the virtual 3-D model to accurately determine a position and orientation of the dental tool relative to the virtual 3-D model of the dental arch.

In some embodiments, the tool identifier 170 may include tool profiles that are usable to identify particular dental tools in the image data 162. A tool profile for a particular tool or input device may include the geometrical configuration of the particular tool and/or a tool identifier associated with that tool. Based on the tool profiles, tool identifier 170 may determine a type of tool, a position of the tool and/or an orientation of the tool. The outcome simulator 176 may use information about the type and position of a tool to determine how a user is changing a treatment outcome.

The treatment planning module 120 may update a treatment outcome based on interactions of an identified tool with a virtual model in a visual overlay of the treatment outcome. For instance, when a tool is in a position corresponding to the virtual position of a tooth in a virtual 3D model of the dental arch, the treatment planning module 120 may track the movement of the tool to determine a corresponding change to the tooth. The treatment planning module 120 may then determine an update to the treatment outcome based on the change to the tooth. If the tooth is touching another tooth, then moving the one tooth may also cause the adjacent tooth to also move. If the tool is interacting with a particular element of the treatment outcome, such as a tooth, a gum line, or another feature, the changes to the position of the tool may be used to change the position of the element in the treatment outcome. Thus, if the tool pushes, pulls, rotates, or otherwise changes position of the element, the element of the treatment outcome that the tool is interacting with may change position or orientation accordingly. In some embodiments, the treatment planning module 120 may update other elements of the treatment outcome as necessary to enable the update. For example, other teeth may be moved in response to an update to a first tooth indicated by tool.

In one embodiment, virtual interface module 121 includes a haptics module 177. A dental practitioner may wear haptics gloves that are capable of providing forces, vibrations and/or motions to the dental practitioner. Alternatively, or additionally, a stylus, pointer, or other instrument used by the dental practitioner or patient may include haptics components that can provide such forces, vibrations and/or motions. The outcome simulator 176 may provide indications to the haptics module 177 about the state of changes to the treatment outcome as it is updated by a user. For instance, the outcome simulator 176 may provide an indication to the haptics module 177 when an update to the treatment outcome is proposed by a user. For example, when user input is received that indicates a position of a tip of a haptics pointer or stylus has touched a tooth, then a haptic feedback may be generated to provide a touch sensation. Different haptic feedback may be provided when the haptics device interfaces with hard elements (e.g., teeth) vs. soft elements (e.g., gums) in the virtual 2D or 3D model of the dental arch. The haptic gloves and/or dental tool may then provide a force, vibration or motion to indicate a status of a change to the treatment outcome and/or the interaction with the virtual 2D or 3D model represented in the visual overlay 164.

In some embodiments, the outcome simulator 176 may determine a status of a change to a treatment plan based on the rules used by the outcome simulator. The outcome simulator 176 may provide a first signal to the haptics module 177 to provide a first feedback level or sensation when a user first interacts with an element of a treatment outcome. For example, haptic feedback may be provided when a user begins to change the position of a tooth. A second haptic feedback level may be provided if the user attempts to position the tooth in an invalid position or if the user attempts to move a tooth through another tooth. Other levels of haptic feedback may also be provided based on other changes to the treatment outcome.

In one embodiment, AR processing module 108 includes medical record interface module 192. Medical record interface module 192 is responsible for automatically retrieving patient data for a particular patient when appropriate. Medical record interface module 192 may include a medical record identification module 193 and a data (e.g., dental data) retriever 194.

Medical record identification module 193 searches within image data 162 for a patient identifier. Once a patient identifier is detected within image data 162, medical record identification module 193 invokes data retriever 194, which retrieves patient data (e.g., dental data) using the patient identifier. Data retriever 194 may make a query to a database that stores the patient data 188. The query may include the patient identifier as a key. The database may then respond by sending patient data such as x-rays, images, patient history, virtual 3D models, etc. to AR processing module 108.

FIGS. 2-13 below describe example applications of AR enhancements for a dental practitioner or patient. The examples are described with reference to images representing an AR display provided to a dental practitioner or patient and/or flow charts describing processes of generating or providing such AR displays. In addition, the flow charts provide example processes that may be performed by an AR system. However, the processes performed by the AR system may include fewer or additional blocks than shown, and in some embodiments the processes in the flow charts may be performed in a different order than shown.

The methods depicted in FIGS. 2-13 may be performed by a processing logic that may comprise hardware (e.g., circuitry, dedicated logic, programmable logic, microcode, etc.), software (e.g., instructions run on a processing device to perform hardware simulation), or a combination thereof. Various embodiments may be performed by an AR system 100, a computing device 105 and/or an AR processing module 108 as described with reference to FIGS. 1A-1B.

Figure 2:
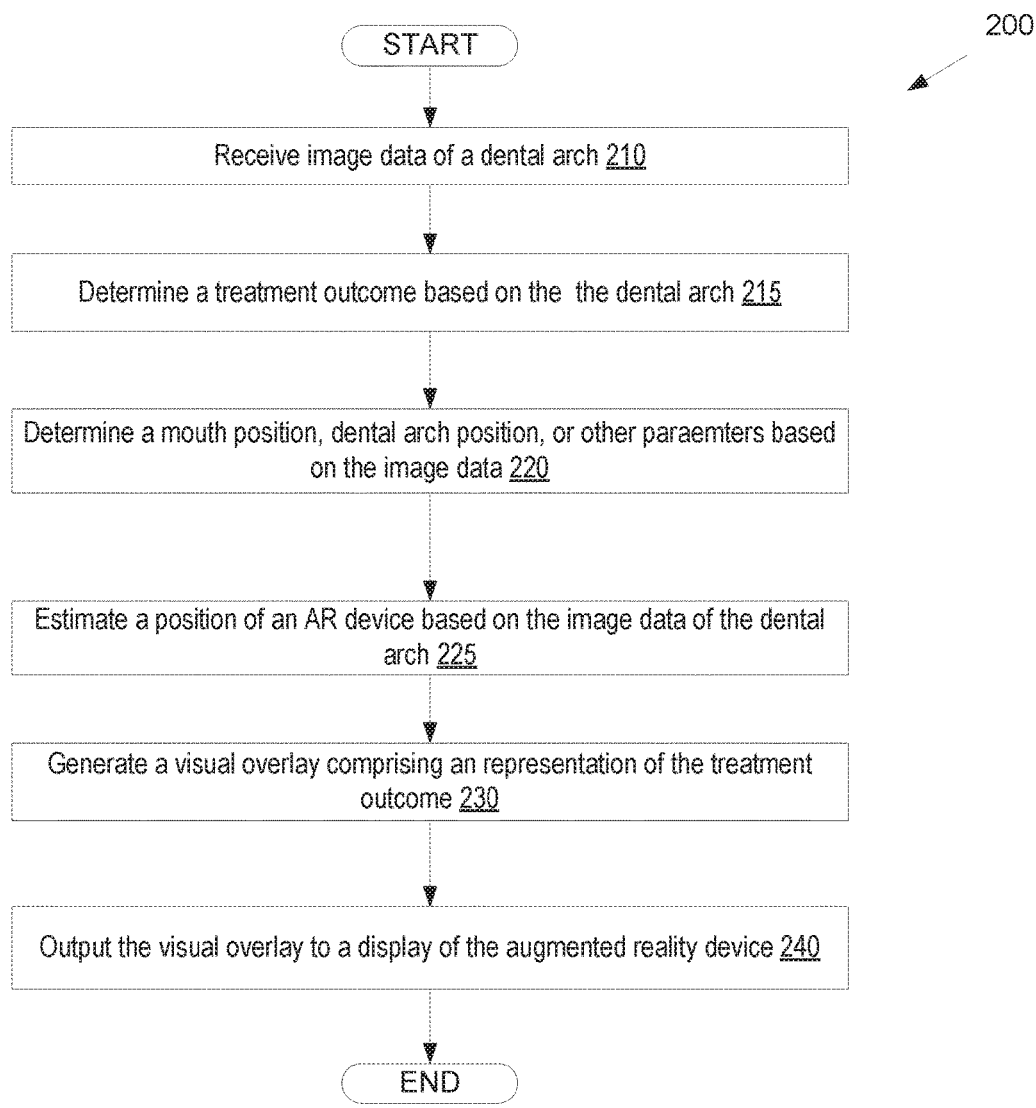
FIG. 2 illustrates a flow diagram for a method of providing a visual overlay of a treatment outcome by an augmented reality device, in accordance with an embodiment.

FIG. 2 illustrates a flow diagram for a method 200 of providing a treatment outcome as a visual overlay, in accordance with an embodiment. At block 210 of method 200, processing logic receives image data of a dental arch from an image capture device of an augmented reality system.

At block 215, processing logic determines a treatment outcome based on the dental arch. In some embodiments, the treatment outcome may be based directly on the image data received in block 210. In some embodiments, the treatment outcome may be based on other information such as a 3D model or scanned image data associated with a patient. The treatment outcome may be, for example an orthodontic treatment outcome that shows a person's teeth in a straightened and aligned arrangement. In one embodiment, the treatment outcome may have already been determined based on performing an intraoral scan of the patient's oral cavity, generating an initial virtual 3D model of the patient's dental arches, and then generating a final virtual 3D model of the target dental arches for the patient as they will be after orthodontic treatment. Alternatively, the treatment outcome may be a potential treatment outcome that may be computed automatically based on the received image data. The potential treatment outcome may have a lower accuracy, but may provide a good visualization of what the person's teeth might look like after orthodontic treatment or other dental treatment.

At block 220, processing logic determines a position of a mouth, a dental arch, or other parameters based on the image data. For example, the mouth position may be determined relative to the position of an imaging device that is providing image data to the AR device. The dental arch position may also be determined relative to an AR display. Other parameters may include the shape of a mouth or oral cavity, areas of a mouth that are covered by lips of a patient, or additional parameters indicating a position and shape of a patient's mouth. In one embodiment, a focal length and/or field of view (FOV) of the image capture device used to generate the image data is used in determining the position of the mouth and dental arch. The focal length may be known a priori, or may be determined.

Processing logic may determine a perspective of the AR display relative to the position of the dental arch as viewed in the image data. In one embodiment, processing logic generates a plurality of perspective view images of the 3-D model. Processing logic may then compare the image data of the dental arch to the plurality of perspective view images to identify a perspective view image for which the model in the perspective view image most closely matches the dental arch in the image. Processing logic may then determine a portion of the virtual three-dimensional model that would be visible from the perspective of the AR display based on the size and shape of the dental arch that is viewable in the image data.

At block 225, processing logic may estimate an AR display position based on the image data. For example, the position of the image capture device in the AR display may be determined relative to the mouth of a patient. This may be used to determine a placement of an overlay of the determined treatment outcome. In some embodiments, the position of the AR display may also be determined.

In one embodiment, the image data includes an image of the AR display itself (e.g., if the image data is from a user wearing the AR display looking in a mirror). There may be a fixed distance between the AR display and an upper dental arch of the patient or wearer. This fixed distance may be determined based on identifying the AR display and the upper dental arch in the image data and measuring a distance between the AR display and the upper dental arch. There may be a known relationship between a position of the upper dental arch and possible positions of the lower dental arch. Accordingly, once the position of the upper dental arch is known, processing logic may search for the lower dental arch within a narrowed region in the image data based on the known possible positions of the lower dental arch relative to the upper dental arch. The area in the image data to search for the lower arch may be based on a) the fixed distance between the upper arch and the image capture device of the AR display and) a modeled range of motion for the lower arch relative to the upper arch.

At block 240, processing logic generates a visual overlay comprising the determined treatment outcome. The visual overlay may include a two dimensional or three dimensional perspective of the portion of the virtual three-dimensional model that would be visible from the perspective of the AR display. At block 250, processing logic outputs the visual overlay to the AR display. The treatment outcome in the visual overlay is superimposed on the AR display over a view of the dental arch at the determined mouth position. A determined shape of the mouth may be used to determine a shape of the overlay of the treatment outcome.

Method 200 may be performed by a computing device of a user at the user's home without the user having to visit a dentist office. For example, the user may download a program that includes an AR processing module. The user may indicate a brand of AR display that the user owns, and may then wear the AR display while looking in a mirror and smiling at home. Method 200 may then be performed by the AR processing module executing on the user's home computing device. The user may alternatively install the program for the AR processing module on a computing device (e.g., a tablet computer or mobile phone) that includes an image capture device and a display. The image capture device may generate a video of the user's face, and the AR processing module may process the video to find the dental arch and replace it with a corrected dental arch, and may output to the display an altered version of the video that includes the corrected dental arch in the user's mouth. In either example, the AR processing module may continue to track the user's mouth and dental arch, and may update the treatment outcome that is shown based on changing lips, changes in the user's smile, movements in the user's head, and so on.

Figure 3:
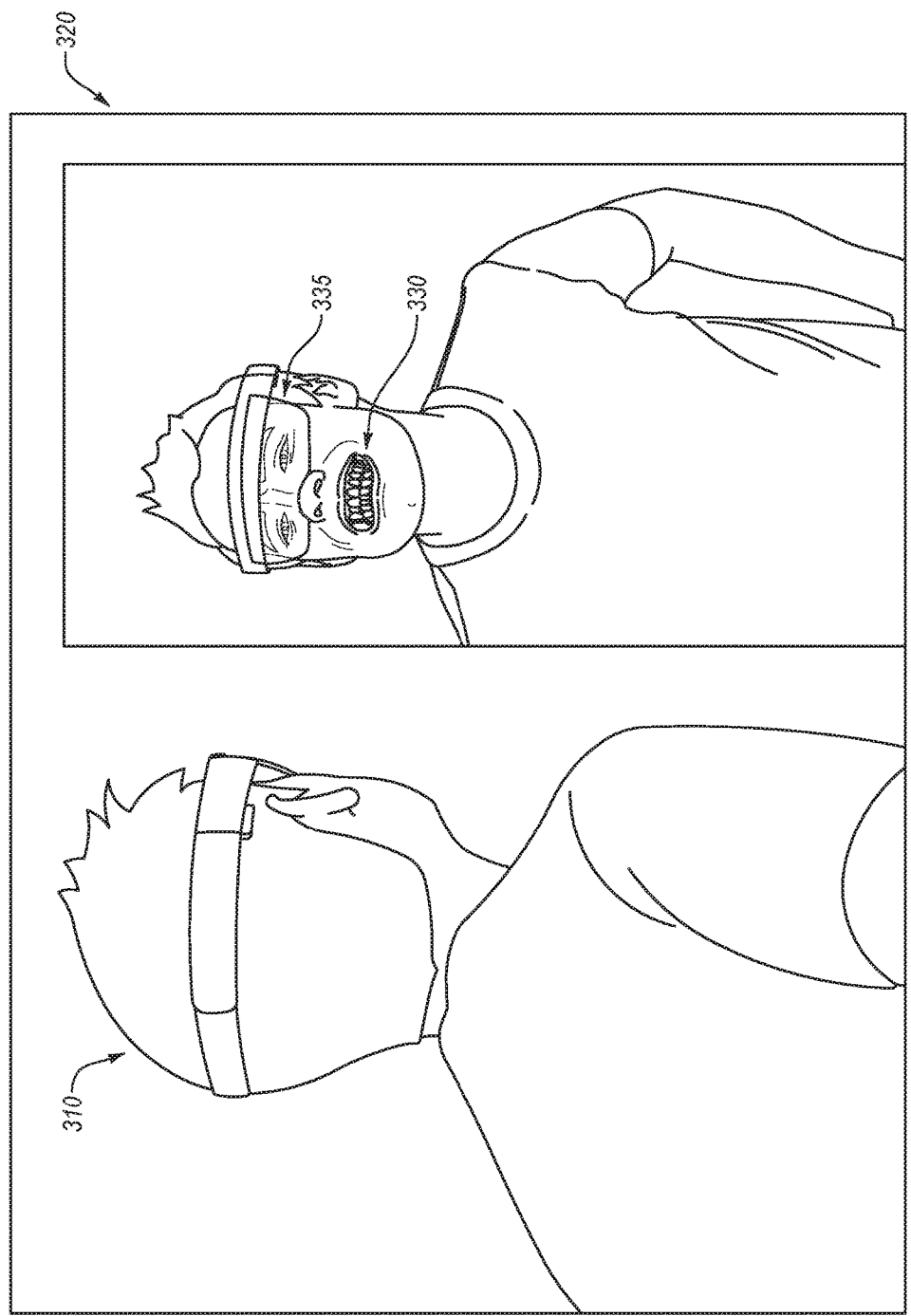
FIG. 3 illustrates a view of an example augmented reality display showing a treatment outcome, in accordance with an embodiment.

In some embodiments, the process described in FIG. 2 may be performed with respect to an AR display device worn by a patient. The treatment outcome may then be used to provide a patient with a view of his own smile after a treatment is performed. FIG. 3 is an example of an AR display 335 that includes a patient viewing a treatment outcome as an overlay 330 on his mouth. In FIG. 3 the patient 310 is viewing a mirror 320. In the mirror 320, the patient 310 may see himself, with a treatment overlay 330 that shows a planned treatment outcome for the patient superimposed over the patient's current dentition. In some embodiments, processing logic may determine a position for the overlay as discussed with reference to FIG. 2. The processing logic may further be configured to update a treatment outcome to appear in reverse to correspond to the orientation of a patient's mouth in a mirror 320. In some embodiments, rather than a mirror 320, the overlay of a treatment outcome 330 may be displayed on a display screen that captures video of a patient 310 and provides a video output with a treatment outcome 330.

Figure 4:
FIG. 4 illustrates a view of an example augmented reality display showing a treatment outcome, in accordance with an embodiment.

FIG. 4 is an example of an AR display that includes a patient viewing a treatment outcome as an overlay 430 on her mouth. In FIG. 3 the patient 410 is viewing an AR display screen 410. In the AR display screen 410, the patient may see herself, with a treatment overlay 430 that shows a planned treatment outcome for the patient. In some embodiments, processing logic may determine a position for the overlay as discussed with reference to FIG. 2. The processing logic may further be configured to provide the treatment outcome based on image data of the patient. In some embodiments, the AR display 410 may be a mobile device, kiosk, or other computing device. The AR display 410 may provide the overlay 430 in response to a request to show a treatment outcome for a patient or potential patient. The treatment outcome may be provided on a live video feed of a patient so that the treatment outcome overlay 430 appears as a natural smile of the patient on the AR display 410. For example, a kiosk may include an image capture device and a display screen. The image capture device may take an image or live video of a smiling person, and the processing logic may generate a visual overlay for the image or video. The image or video may then be displayed with the visual overlay on the display screen. The display screen may additionally include contact information for one or more dental practitioners who can perform orthodontic treatment on the person to achieve the treatment outcome.

Figure 5:
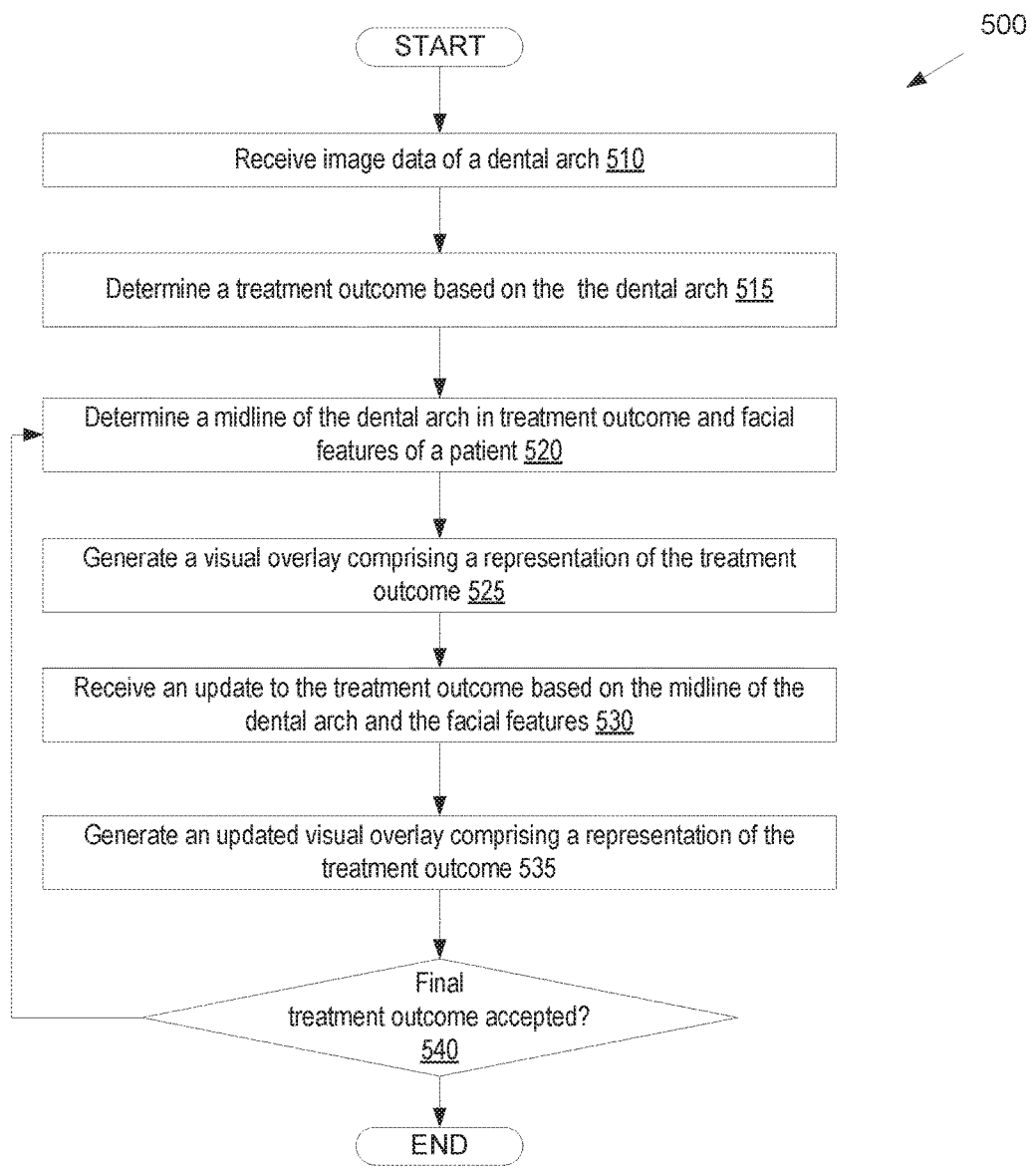
FIG. 5 illustrates a flow diagram for a method of providing a visual overlay of a treatment outcome by an augmented reality device based, in accordance with an embodiment.

FIG. 5 illustrates a flow diagram for a method 500 of updating a treatment outcome based on a midline of a simulated treatment outcome and a midline of a patient's facial features. At block 510, processing logic receives image data of a dental arch from an image capture device of an augmented reality system. At block 515, processing logic determines a treatment outcome based on the dental arch. In some embodiments, the treatment outcome may be based directly on the image data received in block 510. In some embodiments, the treatment outcome may be based on other information such as a virtual 3D model of a final dental arch for the patient or scanned image data associated with the patient.

At block 520, processing logic determines a position of a midline of the dental arch in a treatment outcome and a midline of facial features of a patient. The midline of the dental arch may be determined as a line corresponding to the middle of the two front teeth of the treatment outcome. The midline of features of a patient's face may be determined based on the midpoint between the patient's eyes, the alignment of a patient's nose or chin, the midpoint of other facial features of a patient, or based on other details of a patient's face.

At block 525, processing logic generates a visual overlay comprising the determined treatment outcome. To generate the overlay, processing logic may estimate an AR display position based on the image data. For example, the position of an image capture device of the AR display may be determined relative to the mouth of a patient. This may be used to determine a placement of an overlay of the determined treatment outcome. In some embodiments, the position of the AR display may also be determined. The overlay may include a representation of a dental arch and/or facial midline.

At block 530, processing logic may receive an update to the treatment outcome. For example, processing logic may receive user input that adjusts the midline. The user input may be received via a haptic feedback device interacting with a visual overlay of the treatment outcome. The update to the treatment outcome may be determined from the user input. The update may include a change to a midline of the dental arch. For example, the update may adjust the position of one or more teeth in the patient's mouth to move the midline of the dental arch into or closer to alignment with a midline of the patient's face. In some embodiments, processing logic may receive the update from a dental practitioner or a patient that is viewing the overlay of the treatment outcome. In some embodiments, the treatment outcome may be updated automatically based on the determined midlines.

At block 535, processing logic updates the visual overlay based on the received update to the treatment outcome. For example, if a midline of a dental arch was brought closer to the midline of a patient's face, the treatment outcome may be adjusted with the new midlines and corresponding positions of the patient's teeth. This may include updating a virtual 3D model of a dental arch of the patient.

At block 540, processing logic may determine whether a final treatment outcome is accepted. If a final outcome has not been accepted, the processing logic may return to block 520 to determine new midlines for a patient and further adjust the treatment outcome and visual overlay of the treatment outcome for a patient. If a final outcome has been accepted, the method 500 may end. In some embodiments, a similar process to that described with reference 500 may be used to provide additional updates to a treatment outcome. For instance, alternative to or in addition to providing an indication of midline alignment, processing logic may provide a visual overlay with additional information that may be used to update a treatment outcome. As an example, processing logic may provide an indication that a treatment outcome has a dental arch that is narrow when compared to the shape of a patient's mouth. The indication may be provided by comparing the outer portion of a patient's smile to the outer portion of a patient's dental arch. The visual overlay may then indicate that there is a gap between the positions. If a corresponding update is made to a treatment outcome, the visual overlay may be updated with a corresponding update to the treatment outcome.

Figure 6:
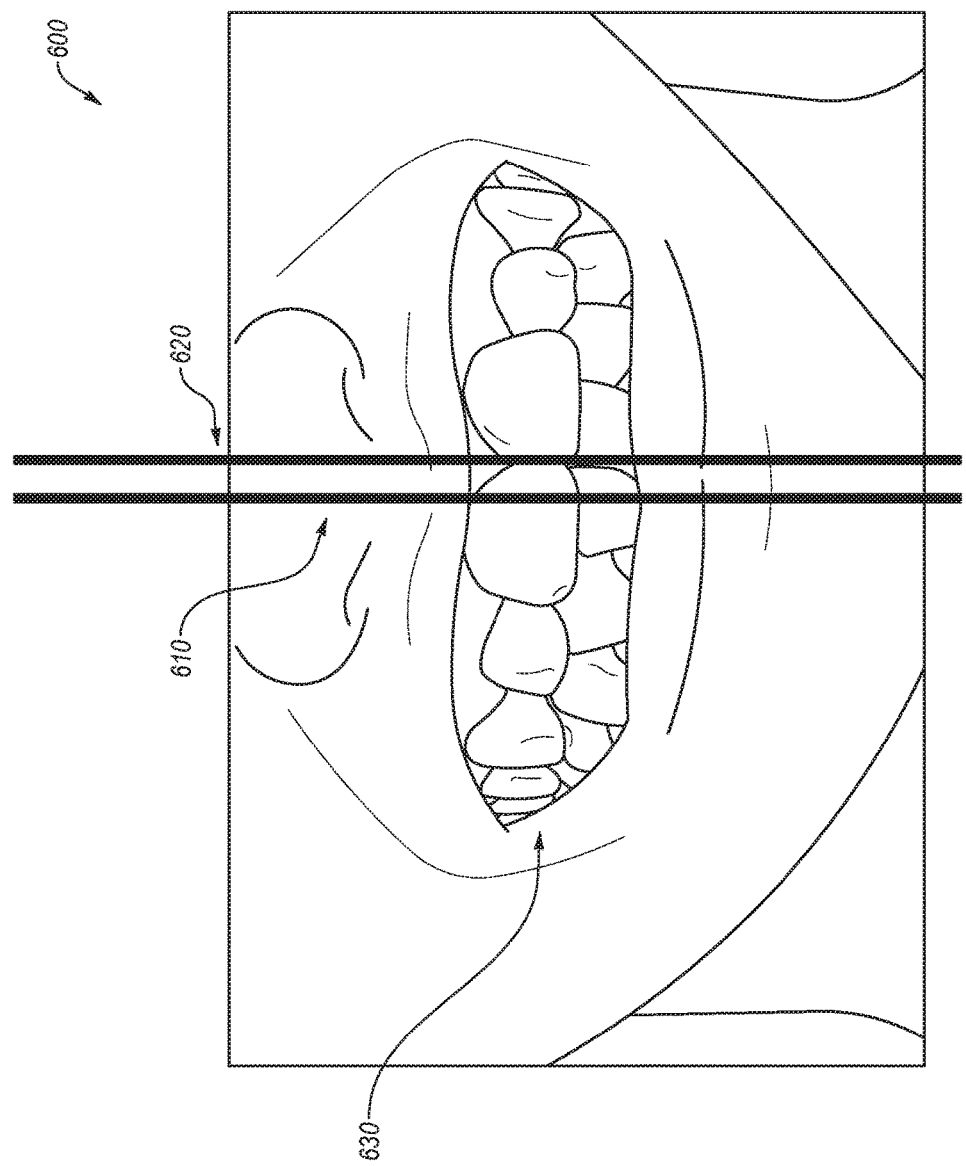
FIG. 6 illustrates a view of an example augmented reality display showing a treatment outcome, in accordance with an embodiment.

FIG. 6 is an example illustration of a portion 600 of a view of an AR display having overlay indicators of a first midline 630 of a patient's dental arch and a second midline 610 of the patient's facial features, according to an embodiment. The example overlay shown in FIG. 6, may be generated accordingly to method 500 described above, for example. In the example overlay, first midline 610 of a patient's face and second midline 620 of a patient's dental arch is shown. The visual overlay 630 may show a treatment outcome that is currently planned for the patient. In the portion of the AR display 600, the midlines 610, 620 are not aligned. Accordingly, after displaying the visual overlay 630, processing logic may receive an indication of an update to the treatment outcome. The update may be received based on user input of the dental practitioner or patient interacting with the visual overlay of the treatment outcome (e.g., touching a virtual 3D model in a VR image using a haptic device). For instance, an update may move the midlines closer to alignment by moving the second midline 620. The processing logic may then update the treatment outcome and the visual overlay of the treatment outcome. New midlines of a patient's face and dental arch may be displayed as a visual overlay. The process of updating the treatment outcome may be repeated until it is accepted by a patient or a dental practitioner.

Figure 7:
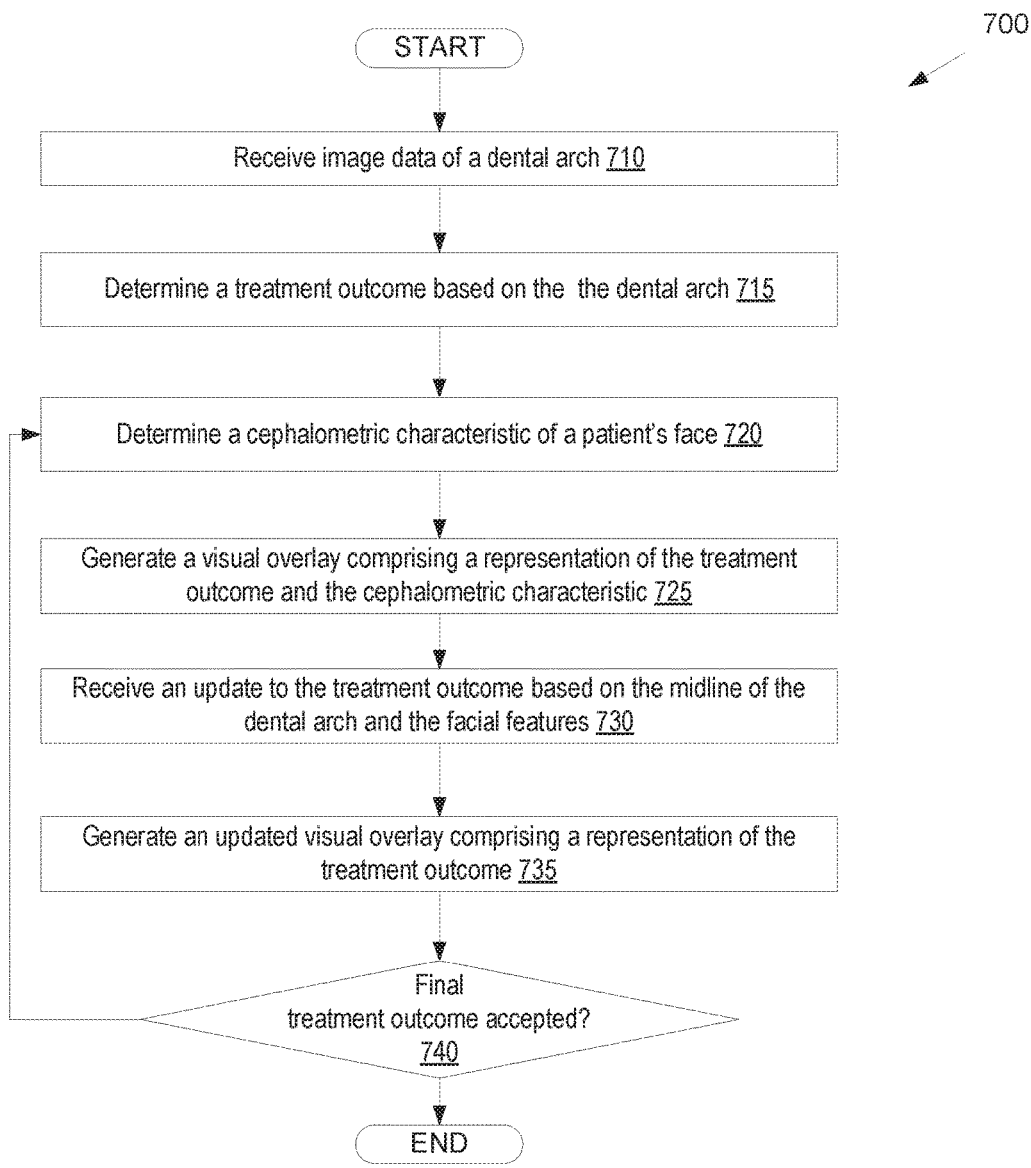
FIG. 7 illustrates a flow diagram for a method of providing a visual overlay of a treatment outcome by an augmented reality device based, in accordance with an embodiment.

FIG. 7 illustrates a flow diagram for a method 700 of updating a treatment outcome based on cephalometric analysis of a patient's facial features. Cephalometric analysis of a patient's facial features may provide information such as alignment of a patient's nose, chin, eyes, ears, and other facial features. As a dental arch is changed for a patient, one or more cephalometric characteristics may also be changed. For example, the position of a patient's chin relative to the patient's nose may change if the position of teeth on the lower jaw and/or the position of the lower jaw itself are changed. A simulated treatment outcome may indicate those changes based on an estimated final position. In the flow diagram of method 700, at block 710 processing logic receives image data of a dental arch from an image capture device of an augmented reality system. At block 715, processing logic determines a treatment outcome based on the dental arch. In some embodiments, the treatment outcome may be based directly on the image data received in block 710. In some embodiments, the treatment outcome may be based on other information such as a 3D model of the dental arch, x-ray data of the dental arch, and/or scanned image data associated with a patient.

At block 720, processing logic determines a cephalometric characteristic of a patient's face. In some embodiments, the cephalometric analysis may be performed based on the image data received at block 710. In some embodiments, the cephalometric analysis may be performed based on x-ray or other scanned image data associated with the patient. The x-ray data may include a cone beam tomography (CBCT) image, a panoramic x-ray image, one or more traditional x-ray images, and the like.

At block 725, processing logic generates a visual overlay comprising the determined treatment outcome. To generate the overlay, processing logic may estimate an AR display position based on the image data. For example, the position of an image capture device of the AR display may be determined relative to the mouth of a patient. This may be used to determine a placement of a visual overlay of the determined treatment outcome. In some embodiments, the position of the AR display may also be determined. The overlay may include a representation of a dental arch and/or facial features.

At block 730, processing logic may receive an update to the treatment outcome. The update may include a change to treatment outcome to change a shape of a dental arch and/or relationship between an upper dental arch and a lower dental arch (e.g., showing a standard bite, overbite, under bite, etc.). The change to the shape of the dental arch and/or relationship between the upper and lower dental arch may change the cephalometric analysis of a simulated treatment outcome. For example, the update may adjust the position of one or more teeth and/or dental arch in the patient's mouth. The change may update the position of a patient's chin relative to the patient's nose. In some embodiments, the processing logic may receive the update from a dental practitioner or a patient that is viewing the visual overlay of the treatment outcome. In some embodiments, the treatment outcome may be updated automatically based on the cephalometric analysis.

At block 735, processing logic updates the visual overlay based on the received update to the treatment outcome. For example, the treatment outcome may be adjusted and a new visual overlay may be generated that has the new treatment outcome and updated cephalometric analysis based on the new treatment outcome.

At block 741, processing logic may determine whether a final treatment outcome is accepted. If a final outcome has not been accepted, the processing logic may return to block 740 to determine new midlines for a patient and further adjust the treatment outcome and visual overlay of the treatment outcome for a patient. If a final outcome has been accepted, the method 700 may end.

Figure 8:
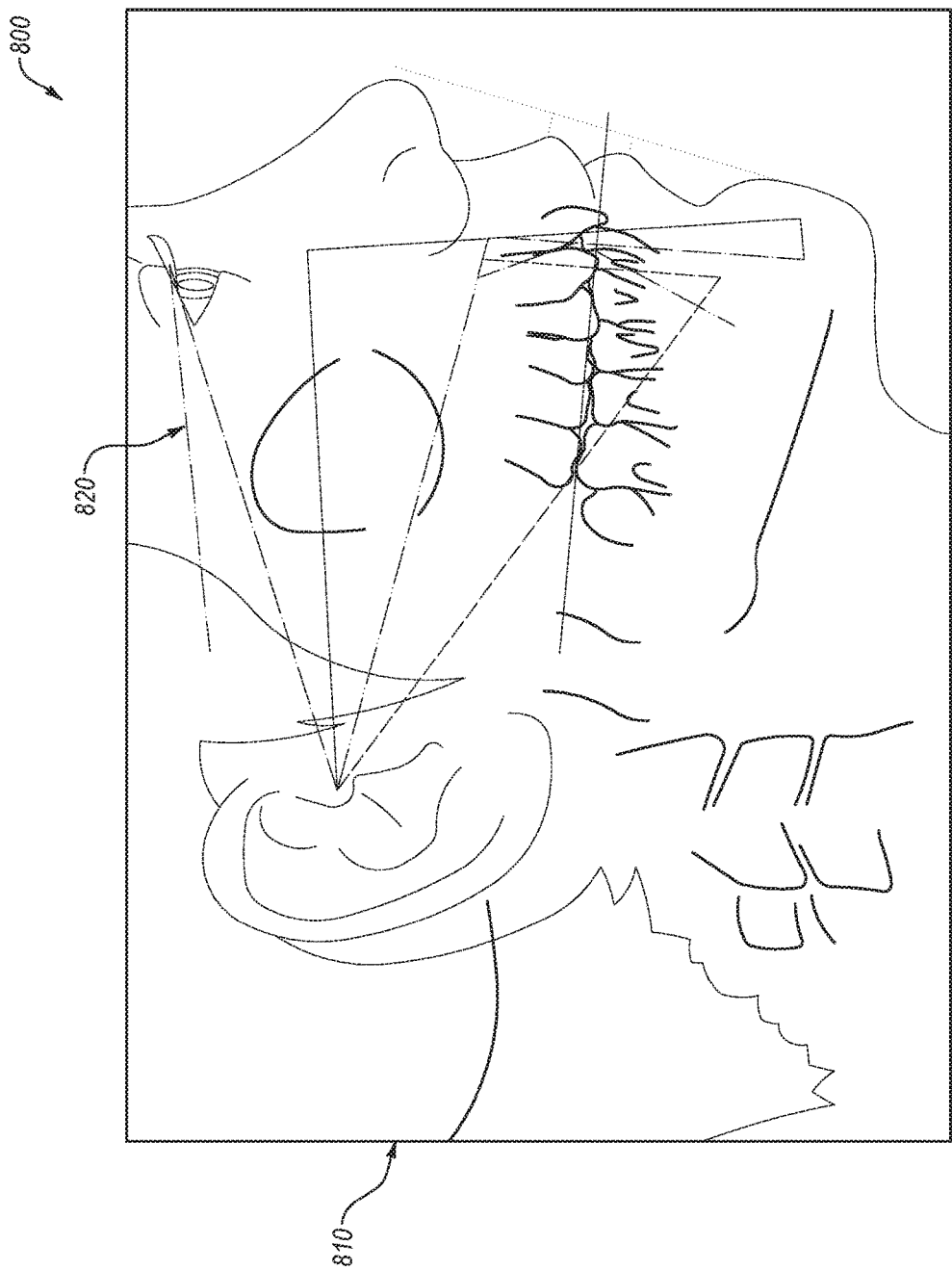
FIG. 8 illustrates a view of an example augmented reality display showing a treatment outcome, in accordance with an embodiment.

FIG. 8 is an example illustration of a portion 600 of a view of an AR display having overlay indicators of a cephalometric analysis performed of a patient's dental arch and facial features, according to an embodiment. The example overlay shown in FIG. 8 may be generated accordingly to method 700 described above, for example. In the example overlay, a patient's face 610 and an overlay 620 of a number of cephalometric characteristics is shown. The overlay 620 may show cephalometric features based on the patient's current dental arch, based on a current treatment outcome, or both a current dental arch and a treatment outcome that is currently planned for the patient. In the portion of the AR display 800, a patient or dental practitioner may determine that after a treatment outcome, one or more cephalometric characteristics may be undesirable. Accordingly, after displaying the visual overlay 820, the processing logic may receive an indication of an update to the treatment outcome. For instance, an update may move the position of one or more teeth to adjust the position of a patient's chin relative to the patient's nose. The update may be received based on user input of the dental practitioner or patient interacting with the visual overlay of the treatment outcome (e.g., touching a virtual 3D model in a VR image using a haptic device). The processing logic may then update the treatment outcome and the visual overlay of the treatment outcome. New cephalometric characteristics of a patient's face and dental arch may be displayed as a visual overlay. The process of updating the treatment outcome may be repeated until it is accepted by a patient or a dental practitioner.

Figure 9:
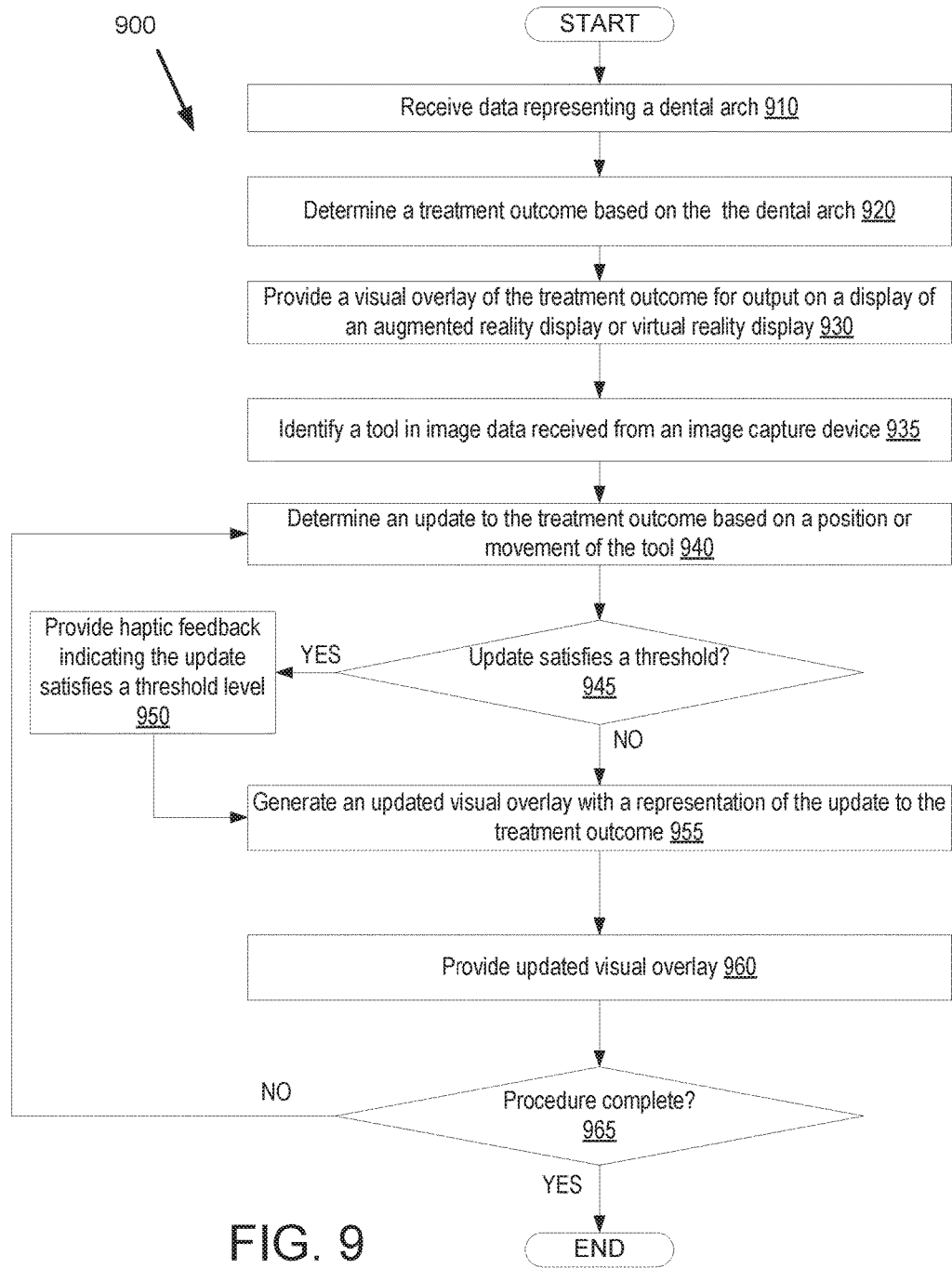
FIG. 9 illustrates a flow diagram for a method of providing a visual overlay of a treatment outcome by an augmented reality device based, in accordance with an embodiment.

FIG. 9 illustrates a flow diagram for a method 900 of providing a visual overlay of a treatment outcome and updating the treatment outcome. In the flow diagram 900, at block 910, processing logic receives data representing a dental arch. The data representing the dental arch may be a virtual 3D model based on an intraoral scan of a patient's dental cavity, image data from an image capture device, x-ray images of the dental arch, and/or other data that provides information about the configuration of features in a patient's dental arch. At block 920, processing logic determines a treatment outcome based on the dental arch. In some embodiments, the treatment outcome may be generated by an AR system and/or treatment planning system, or another computing system, to satisfy a set of idealized parameters for a dental arch.

In one embodiment, the treatment outcome may have already been determined based on performing an intraoral scan of the patient's oral cavity, generating an initial virtual 3D model of the patient's dental arches, and then generating a final virtual 3D model of the target dental arches for the patient as they will be after orthodontic treatment.

At block 930, processing logic provides a visual overlay of the treatment outcome for output on an AR display of an augmented reality system or a VR display of a VR system. In some embodiments, the visual overlay may be provided as a virtual 2D or 3D model of a dental arch (or upper and lower dental arch) showing the treatment outcome. For example, a virtual 3D model of the dental arches showing the treatment outcome may be provided as a visual overlay. The virtual 3D model may be enlarged such that details of the treatment outcome may be more easily seen by a user. The visual overlay may be provided to a dental practitioner so that the practitioner can update a treatment outcome based on additional clinical information. In some embodiments, the overlay may be provided to a patient such that the patient can see a treatment outcome and make any modifications to meet the patient's preferences. In some embodiments, a patient and a dental practitioner may both have an AR display or VR display that provides an overlay for each. The patient and the dental practitioner may both see and interact with a visual overlay simultaneously to design a treatment outcome that satisfies the dental practitioner and the patient.

In some embodiments, image data such as x-ray image data is registered with the virtual 2D or 3D model and displayed together with the virtual 2D or 3D data. For example, a cephalogram, a panoramic x-ray image, a CBCT image, and/or other x-ray image may be used to display bone structure, facial structure and/or root information of teeth in the virtual 2D or 3D model. Additionally, one or more facial photographs may be used to superimpose a virtual 2D or 3D image of the patient's face over the virtual 2D or 3D model of the dental arch. In some instances, the facial photographs may be of the patient smiling. The superposition of a virtual 2D or 3D model of the patient's face and the virtual 2D or 3D model of the patient's dental arches may be used to show dark triangles at the corners of the patient's mouth (e.g., if the patient's dental arch is too narrow for the patient's smile) and/or to show whether the patient will show gums when the patient smiles after the treatment outcome.

At block 935, processing logic identifies a tool in image data received from an image capture device. For example, a tool may be a haptic feedback device, stylus, glove, or other instrument. The processing logic may identify the tool based on the shape, color, or other characteristic of the tool. In some embodiments, the processing logic may track the tool based on a tracker coupled to the tool. In some embodiments, the processing logic may identify the tool based on a visual indicator on the tool. For example, a OR code, a barcode, or another visual indicator may be included on the tool that is identifiable to the AR device. Additionally or alternatively, other types of data may be used to track the tools, such as magnetic data, radiofrequency (RF) data (e.g., using triangulation and time of flight to multiple transmitters or receivers), accelerometer data, gyroscope data, and so on.

At block 940, processing logic may determine an update to the treatment outcome based on a position or movement of the tool. For example, the processing logic may determine that the position of the tool corresponds to a virtual position of the virtual 3D model of the dental arch in the visual overlay of the treatment outcome. An interaction with the tool and the virtual 3D model of the visual overlay of the treatment outcome may indicate an update to the treatment outcome. The interaction of the tool with the virtual 3D model of the dental arch may cause a position, orientation and/or shape of one or more teeth in the dental arch to change. For example, tooth adjustments such as translations, rotations, angulation, extrusion/intrusion, and so on may be made directly with the virtual 3D model. Alternatively, or additionally, the dental practitioner may make adjustments using a combination of hand gestures, voice commands and/or gaze vector tracking. Some examples of hand gestures include pincer gestures with a user's index finger and thumb to select a tooth in a 3D virtual model of a dental arch and/or to move the selected tooth, a tap gesture to select a tooth, a grab and move gesture to change a location of the 3D virtual model, a grab and twist gesture to rotate the 3D virtual model, and so on. Some examples of voice commands include a rotate model voice command, a select treatment stage voice command, an add attachment voice command, a save voice command, an undo voice command, and so on.

Some AR displays such as Microsoft Hololens tracks a user's gaze to determine where a user is looking, and thus determine a user's intent. Gaze may be detected based on head position and orientation rather than eye tracking, though eye tracking may also be used. By tracking gaze (e.g., using the Gaze feature of Microsoft Hololens), processing logic may place a visual cursor in the center of the dental practitioner's view to let the dental practitioner know which tooth they are about to interact with. The dental practitioner could then interact with an individual tooth using hand gestures or voice commands. To move a central incisor 0.1 mm to the left, for example, the dental practitioner would first look at the tooth. Then using an index finger the dental practitioner may gesture a tap-and-hold command followed by a movement command to the left. Or the doctor could simply say "move tooth number eight by point one millimeters to the left" using a voice command. Accordingly, there are numerous ways to interface with the virtual 2D or 3D model of the dental arch.

A change to the virtual 3D model of the dental arch may be used to compute a new treatment outcome. Examples of changes include rotations of one or more teeth, position change of one or more teeth, a change in the bit position for the jaw, a change in the arch width (and thus an increase or reduction in dark triangles at the edges of the patient's mouth during smiles), and so on.

In an example, a haptic feedback glove or stylus may be tracked and when the glove reaches a position of the virtual 3D model in the visual overlay of the treatment outcome, the processing logic may determine that the user is attempting to move a portion or element of the virtual 3D model in the treatment outcome that the haptic feedback glove or stylus is touching. In some embodiments, the processing logic may also receive other input indicating the change. For instance, a button or other interactive element of the tool may provide input to the processing logic in response to an interaction from the user. The processing logic may then determine based on the input that the user is making a change to the treatment outcome.

At block 945, the processing logic may determine whether an update to the virtual 3D model and/or treatment outcome satisfies a threshold. The threshold may be an initial interaction with the virtual 3D model, an amount of movement of an element of the virtual 3D model, an interaction of an element moved in the virtual 3D model with other elements of the virtual 3D model or the like. For example, the threshold may be set such that it is satisfied if a treatment outcome rule is violated or an update to the treatment outcome would result in an invalid outcome. If the threshold is satisfied, the processing logic may proceed to block 950 and provide haptic feedback indicating that the update satisfies the threshold. In some embodiments, the processing logic may determine if an update to a treatment outcome satisfies more than one threshold. For example, there may be multiple thresholds with a first threshold indicating a first interaction with an element of a virtual 3D model of a dental arch, a second threshold indicating a movement of the element, and a third threshold indicating that the element has been moved a maximum amount or to an invalid position. In various embodiments, different haptic feedback may be provided in response to different interactions of a user with a virtual 3D model and/or treatment outcome in a visual overlay.

At block 955, processing logic updates the visual overlay based on the received update to the virtual 3D model and/or treatment outcome. Additionally, the virtual 2D or 3D model of the patient's face may be updated, and a smile of the patient may be updated based on a superposition of the updated virtual 2D or 3D model of the dental arch and the updated virtual 2D or 3D model of the patient's face. For example, the treatment outcome may be adjusted and a new visual overlay may be generated that has the new treatment outcome and updated cephalometric analysis based on the new treatment outcome. At block 960, the updated visual overlay may be provided to the AR display.

At block 965, the processing logic may determine whether a final outcome has been accepted. If the treatment outcome has not been accepted, the processing logic may return to block 940 to determine new midlines for a patient and further adjust the treatment outcome and visual overlay of the treatment outcome for a patient. If a final outcome has been accepted, the method 900 may end.

Method 900 has been described with reference to visualizing a treatment outcome. However, method 900 may also be used to visualize an intermediate treatment stage in a multi-stage treatment. For example, orthodontic treatment often includes multiple treatment stages, where each treatment stage may have a different target dental arch. A virtual 2D or 3D model of the dental arch may be generated for each treatment stage, and method 900 may be used to visualize and adjust the virtual 2D or 3D dental arch of any treatment stage.

Additionally, a dental practitioner and a patient may both wear an AR display or VR display and view the same treatment outcome or treatment stage. The patient and dental practitioner may walk around the virtual 3D model of the dental arch, and the dental practitioner may show the patient the staging of tooth movements and final tooth position. The dental practitioner may walk the patient step-by-step through each stage of treatment using hand gestures and/or voice commands to switch between treatment stages shown and/or adjust a view of the virtual 3D model for a treatment stage.

The patient may also be shown a virtual 3D model of the patient's current dental arch (e.g., pre-treatment). Any imperfections of the patient's dental arch may be highlighted so that the dental practitioner can call them to the attention of the patient. The patient may be able to touch their teeth, push and rotate them as they want, and so on.

Method 900 may be performed by a patient after a treatment plan has been generated for that patient. The patient may then adjust the treatment outcome based on that patient's own aesthetics. The patient may have customized options for moving final tooth positions, making teeth slightly crooked, adding a small gap between teeth, and so on. The changes that the patient is allowed to make may be limited to changes that are not clinically significant (e.g., changes that will not introduce a malocclusion, interfering contacts, and so on. Accordingly, any changes that are for health reasons of the patient may not be interfered with. However, the patient may be able to adjust aesthetic aspects of the treatment outcome. This may empower the patient so that they feel that they are in control and have the power to rearrange their teeth to the results that they would like.

Figure 10:
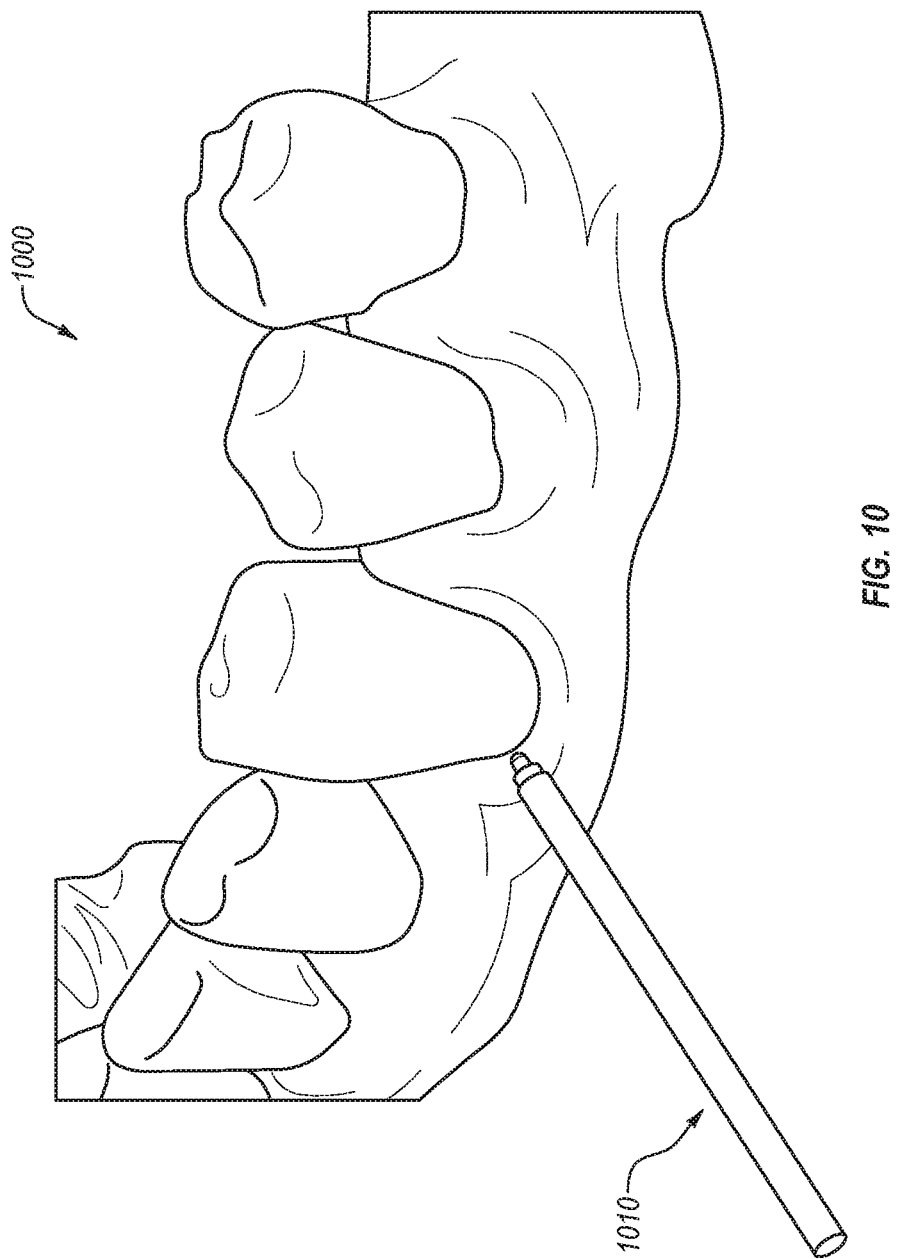
FIG. 10 illustrates a view of an example augmented reality display showing a treatment outcome, in accordance with an embodiment.

FIG. 10 is an example illustration of a portion 1000 of a view of an AR display showing a treatment outcome, according to an embodiment. The treatment outcome may include all or a portion of a patient's dental arch. As shown in the AR display, the treatment outcome may be a 3D model. A user may interact with the 3D model to update the treatment outcome. In an example, the user may interact with the 3D model using a haptic feedback device 1010. The haptic feedback device 1010 may interact with the 3D model as it approaches a position corresponding to a virtual position of the visual overlay of the treatment outcome. Additionally, the tooth that the haptic feedback device 1010 interacts with may be modified based on the interaction. In response to the haptic feedback device 1010 interacting with the visual overlay of the virtual 3D model of the treatment outcome, the virtual 3D model and treatment outcome may be modified. The process of updating the treatment outcome may be repeated until it is accepted by a patient or a dental practitioner.

Figure 11:
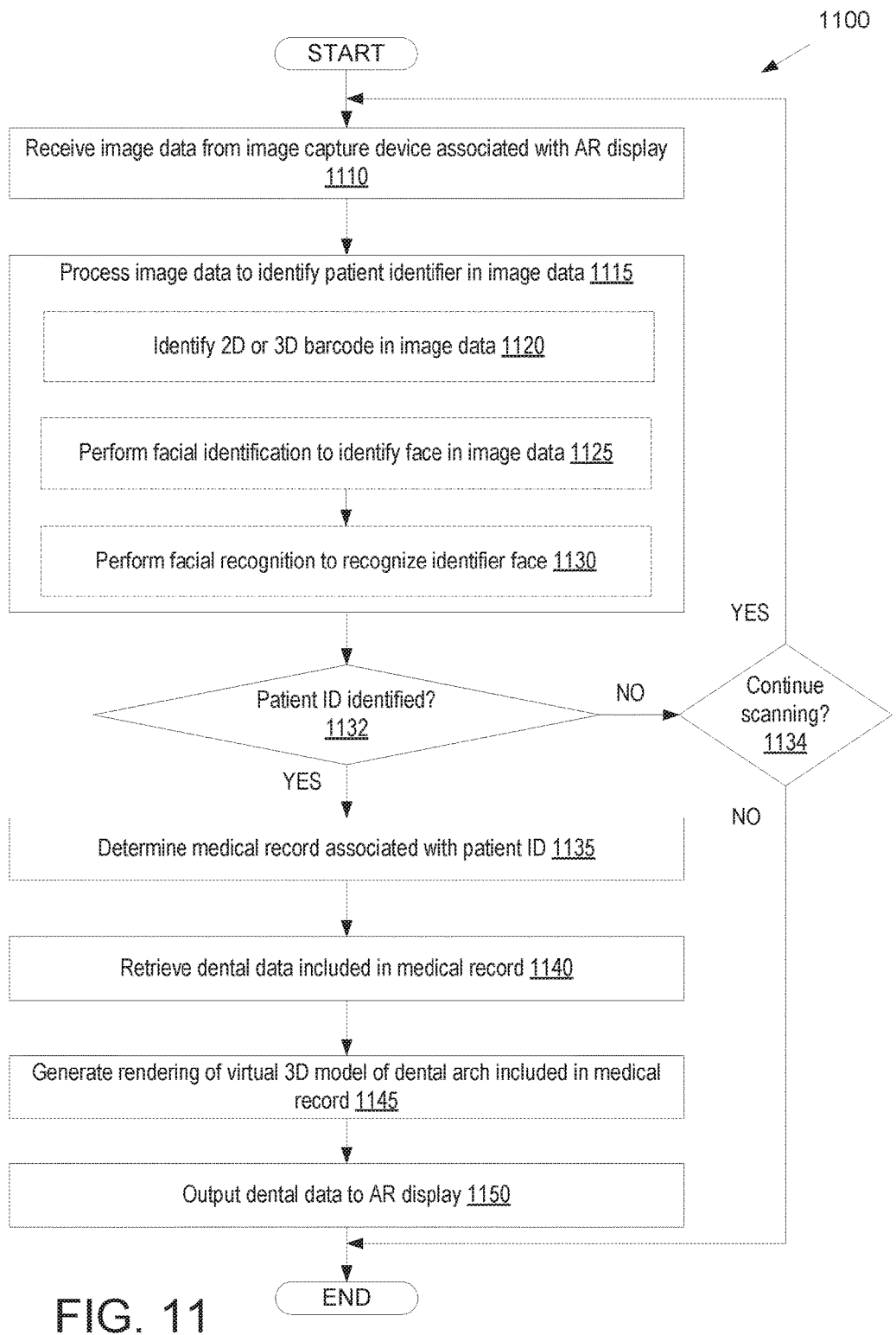
FIG. 11 illustrates a flow diagram for a method of using an AR device to retrieve dental data, in accordance with an embodiment.

FIG. 11 illustrates a flow diagram for a method 1100 of using an AR device to retrieve dental data, in accordance with an embodiment. Method 1100 may be started by a user launching an application or program, or by a user pressing a scan or identify button, for example. At block 1110 of method 1100, processing logic receives image data from an image capture device associated with an AR display. At block 1115, processing logic processes the image data to identify a patient identifier in the image data. The patient identifier may be a unique pattern usable to identify a patient. In one embodiment, the patient identifier is a 2D or 3D barcode. In such an embodiment, at block 1120 processing logic identifies the 2D or 3D barcode in the image data. For example, processing logic may perform object detection to identify a barcode, and may then apply a barcode reader logic to convert the barcode into a numerical value. Alternatively, the patient identifier may be a numerical, alphanumerical or textual value, which may be identified using object identification techniques that look for numbers in the images. In one embodiment, the patient identifier is an image. The image may be a unique image that has been associated with a patient. The unique image may be any type of image, such as an image of a cat, a dog, a tree, a house, and so on. In one embodiment, a feature vector of the image is generated, and the feature vector is used as the patient identifier and sent to a data store for searching the data store for a particular medical record associated with a matching feature vector. Alternatively, the image may be an image of a patient's face. In such an embodiment, at block 1125 processing logic performs facial identification as known in the art to identify a face in the image data. Processing logic then performs facial recognition as known in the art to recognize the identified face as being a particular face. The recognized face may be used to identify a specific medical record associated with a particular patient face.

At block 1132, processing logic determines whether a patient identifier was detected in the image data. If a patient identifier was detected, the method continues to block 1135. If no patient identifier was detected, the method continues to block 1134. At block 1134, processing logic determines whether to continues scanning for a patient identifier. A user may select to continue scanning or to terminate scanning, for example. If processing logic determines to continues scanning, the method returns to block 1110. If processing logic determines to terminate scanning the method ends.

At block 1135, processing logic determines a medical record associated with the patient ID. At block 1140, processing logic retrieves dental data (or other patient data) included in the medical record. In one embodiment, processing logic makes a query to a medical record database using the patient identifier as a key. For example, an API for a medical record database may be used to search the medical record database using the patient identifier. A response to the query may be an indication that the patient identifier is associated with a medical record as well as patient data included in the medical record. In one embodiment, processing logic receives a list of the available patient data, and processing logic selects some or all of the patient data based on user selection.

The patient data may include a virtual 3D model of a dental arch for the patient. At block 1145, processing logic generates a rendering of the virtual 3D model. At block 1150, processing logic outputs the patient data (dental data) to the AR display. This may include outputting the rendering of the virtual 3D model to the AR display. The patient data may be output as a visual overlay that is projected onto a lens of the AR display.

Figure 12:
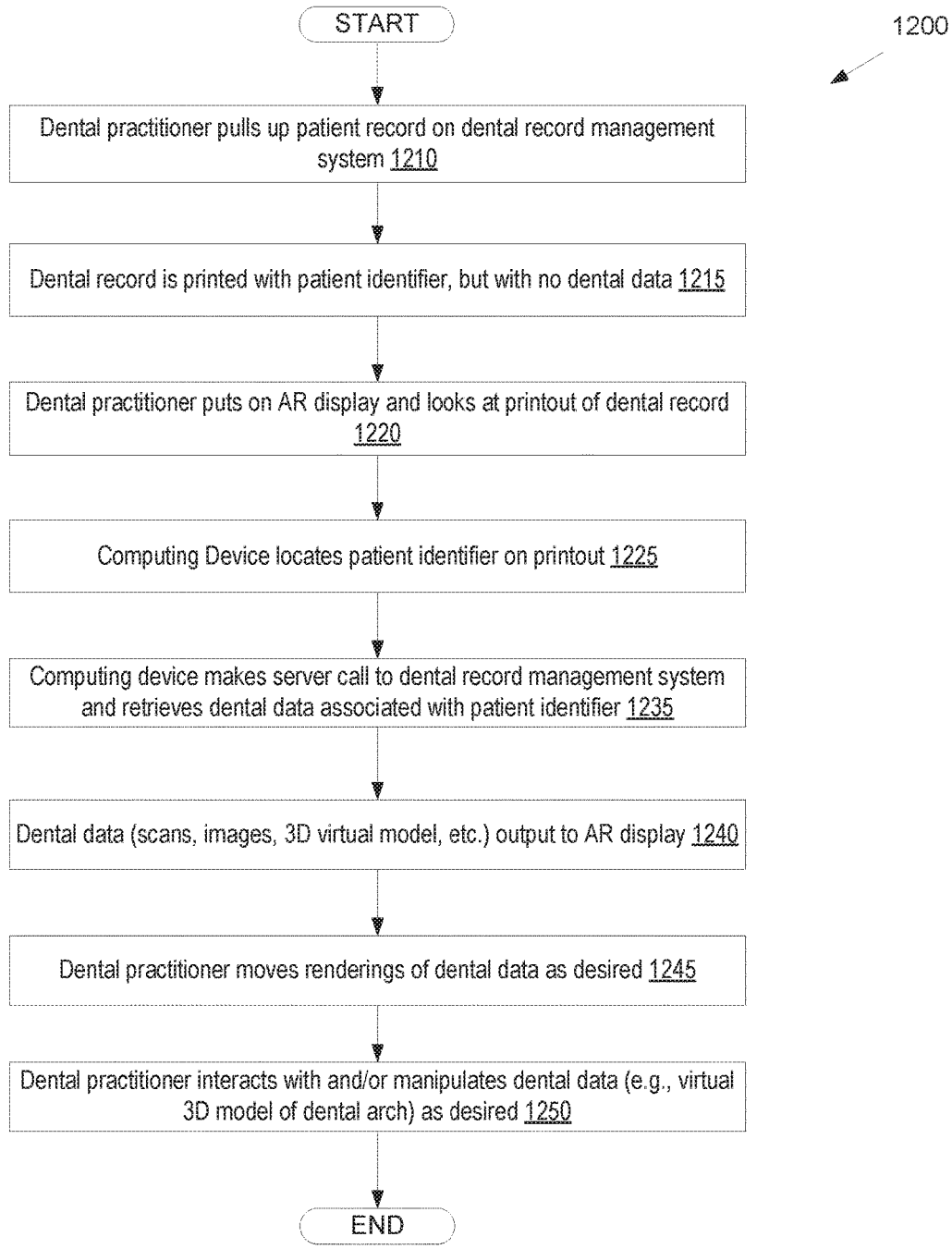
FIG. 12 illustrates a flow diagram for a method of using an AR device to retrieve dental data and interact with the dental data, in accordance with an embodiment.

FIG. 12 illustrates a flow diagram for a method 1200 of using an AR device to retrieve dental data and interact with the dental data, in accordance with an embodiment. At block 1210, a dental practitioner pulls up a patient record (medical record for a patient) on a dental record management system (e.g., a medical record database). At block 1215, the dental record is printed with a patient identifier, but with no dental data. The printout may be on a piece of paper or on a screen of a device such as a tablet computer, a desktop computer, a mobile phone, a laptop computer, etc. Anyone looking at the printout will see the patient identifier, but will not see, for example, a patient name, age, gender, dental data, etc.

At block 1220, the dental practitioner puts on an AR display and looks at the printout of the dental record (the printout with the patient identifier). At block 1225, a computing device of the AR display or a computing device in communication with the AR display searches image data from the AR display and locates the patient identifier on the printout. At block 1235, the computing device makes a server call to the dental record management system and retrieves dental data associated with the patient identifier. The dental data (e.g., scans, images, a 3D virtual model, other patient information, etc.) is then output to the AR display. This enables the dental practitioner to view the dental data after viewing the patient identifier. However, no one else seeing the dental record (printout) would be able to view any of the dental data. Dental data may be repositioned using an input device with a button for dragging and dropping, using voice commands, using gesture commends (with a user's hands or an input device), and so on.

At block 1245, the dental practitioner may move or reposition renderings of the dental data that are shown in the AR display. The dental practitioner may move dental data about within the FOV of the AR display and/or may position some or all of the dental data outside of the FOV of the AR display. The dental practitioner may turn their head to change the area in the FOV to view the dental data.

At block 1250, the dental practitioner may interact with the dental data and/or manipulate the dental data (e.g., a 3D model of a dental arch) as desired. Such interaction may be via a haptics device, voice commands, hand gestures, and so on. In one embodiment, the 3D model of the dental arch is mapped or locked to an object in the FOV of the AR display. The dental practitioner may manipulate the object to change the position and/or orientation of the 3D model. For example, the dental practitioner may rotate the object to cause the 3D model to also rotate.

Figure 13:
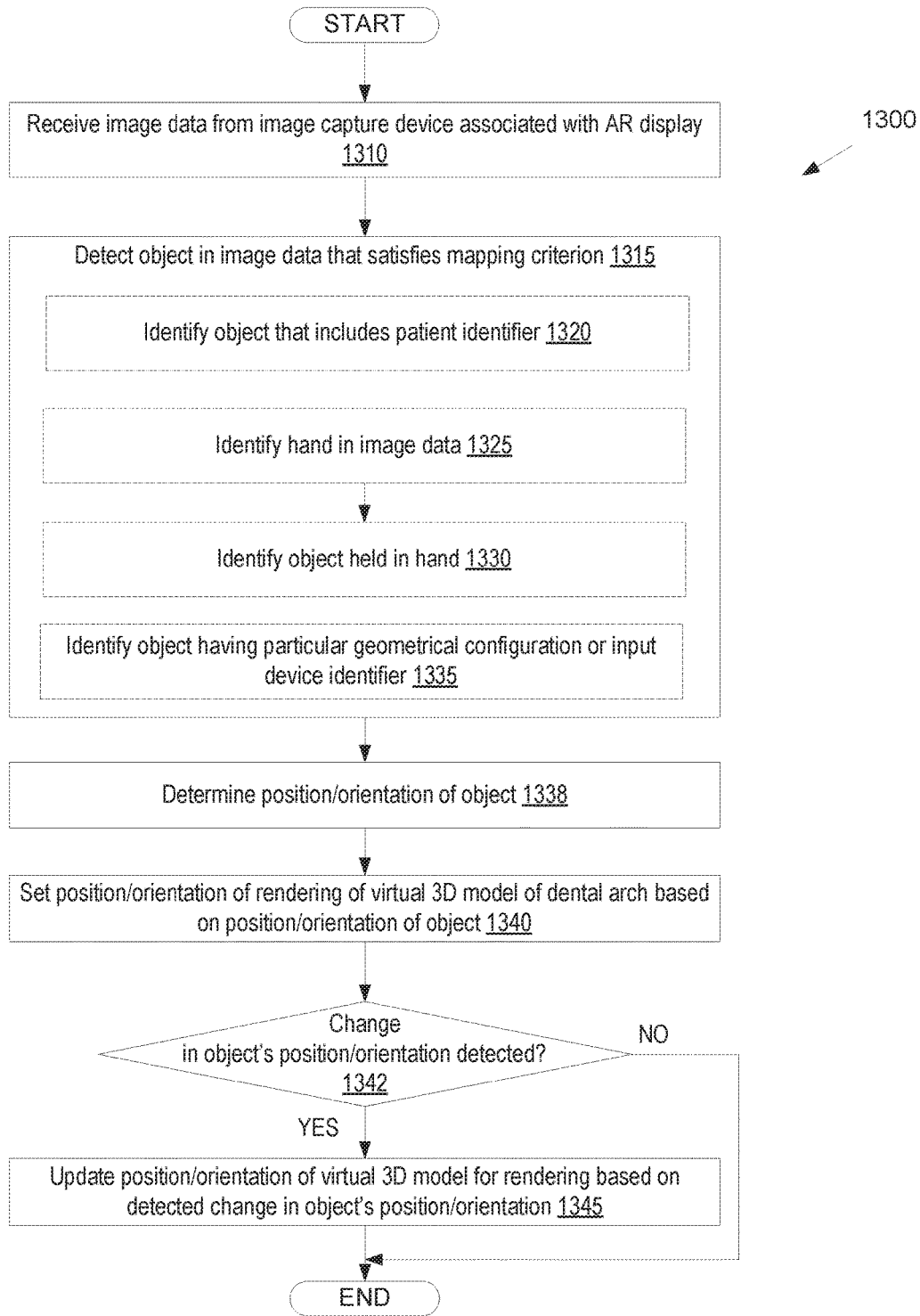
FIG. 13 illustrates a flow diagram for a method of using an object to control the position and orientation of a virtual 3D model of a dental arch that is displayed in an AR display, in accordance with an embodiment.

FIG. 13 illustrates a flow diagram for a method 1300 of using an object to control the position and orientation of a virtual 3D model of a dental arch that is displayed in an AR display, in accordance with an embodiment. At block 1310 of method 1300, processing logic receives image data from an image capture device associated with an AR display. At block 1315, processing logic detects an object in the image data that satisfies a mapping or locking criterion. In one embodiment, the object includes a patient identifier, and processing logic detects the patient identifier in the object at block 1320. In one embodiment, the object includes a user input identifier, which may be similar to a patient identifier but may be associated with a type of input device rather than with a medical record. In one embodiment, the object is held in a user hand. In one embodiment, at block 1325 processing logic performs object identification to identify a hand of a user in the image data. Processing logic then performs object identification to identify an object in the hand. Processing logic may then record a shape of the object in the hand. In one embodiment, image processing is performed to identify an object in the image data that has a particular known geometrical configuration (e.g., a particular size and shape). The particular geometrical configuration may be associated with a known input device.

At block 1338, processing logic determines a position and/or orientation of the object. Alternatively, or additionally, processing logic may determine a position and/or orientation of a patient identifier or input device identifier on the object. At block 1340, processing logic maps or locks the position and/or orientation of the object to the position and/or orientation of a rendering of a virtual 3D model. Accordingly, processing logic sets a position and/or orientation of the rendering of the virtual 3D model based on the position and/or orientation of the object.

At block 1342, processing logic determines whether the position and/or orientation of the object has changed. If so, the method continues to block 1345. At block 1345, processing logic updates the position and/or orientation of the virtual 3D model for rendering based on the detected change in the objects position and/or orientation. For example, if the object that is mapped to the virtual 3D model is a piece of paper with a patient ID printed thereon, then rotating the paper may cause a rendering of the virtual 3D model to similarly rotate.

Figure 14:
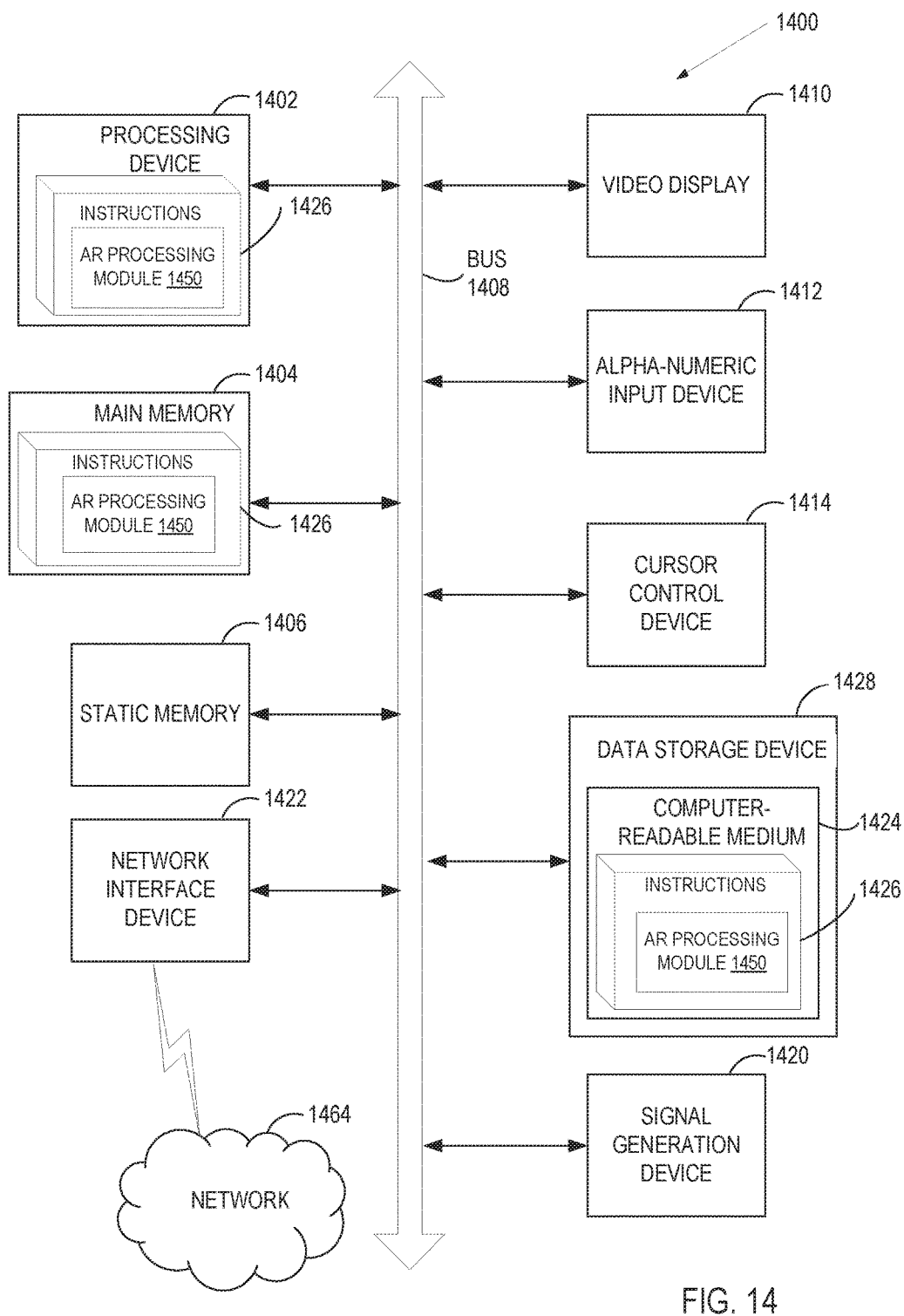
FIG. 14 illustrates a block diagram of an example computing device, in accordance with embodiments of the present invention.

FIG. 14 illustrates a diagrammatic representation of a machine in the example form of a computing device 1400 within which a set of instructions, for causing the machine to perform any one or more of the methodologies discussed herein, may be executed. In alternative embodiments, the machine may be connected (e.g., networked) to other machines in a Local Area Network (LAN), an intranet, an extranet, or the Internet. The machine may operate in the capacity of a server or a client machine in a client-server network environment, or as a peer machine in a peer-to-peer (or distributed) network environment. The machine may be a personal computer (PC), a tablet computer, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein. In one embodiment, the computer device 1400 corresponds to computing devices 105 of FIG. 1A.

The example computing device 1400 includes a processing device 1402, a main memory 1404 (e.g., read-only memory (ROM), flash memory, dynamic random access memory (DRAM) such as synchronous DRAM (SDRAM), etc.), a static memory 1406 (e.g., flash memory, static random access memory (SRAM), etc.), and a secondary memory (e.g., a data storage device 1428), which communicate with each other via a bus 1408.

Processing device 1402 represents one or more general-purpose processors such as a microprocessor, central processing unit, or the like. More particularly, the processing device 1402 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processing device 1402 may also be one or more special-purpose processing devices such as an application specific integrated circuit (ASIC), a field programmable gate array (FPGA), a digital signal processor (DSP), network processor, or the like. Processing device 1402 is configured to execute the processing logic (instructions 1426) for performing operations and steps discussed herein.

The computing device 1400 may further include a network interface device 1422 for communicating with a network 1464. The computing device 1400 also may include a video display unit 1410 (e.g., a liquid crystal display (LCD) or a cathode ray tube (CRT)), an alphanumeric input device 1412 (e.g., a keyboard), a cursor control device 1414 (e.g., a mouse), and a signal generation device 1420 (e.g., a speaker).

The data storage device 1428 may include a machine-readable storage medium (or more specifically a non-transitory computer-readable storage medium) 1424 on which is stored one or more sets of instructions 1426 embodying any one or more of the methodologies or functions described herein, such as instructions for an AR processing module 1450. A non-transitory storage medium refers to a storage medium other than a carrier wave. The instructions 1426 may also reside, completely or at least partially, within the main memory 1404 and/or within the processing device 1402 during execution thereof by the computer device 1400, the main memory 1404 and the processing device 1402 also constituting computer-readable storage media.

The computer-readable storage medium 1424 may also be used to store an AR processing module 1450, which may correspond to the similarly named component of FIGS. 1A-1B. The computer readable storage medium 1424 may also store a software library containing methods for an AR processing module 1450. While the computer-readable storage medium 1424 is shown in an example embodiment to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium other than a carrier wave that is capable of storing or encoding a set of instructions for execution by the machine and that cause the machine to perform any one or more of the methodologies of the present invention. The term "computer-readable storage medium" shall accordingly be taken to include, but not be limited to, solid-state memories, and optical and magnetic media.

It is to be understood that the above description is intended to be illustrative, and not restrictive. Many other embodiments will be apparent upon reading and understanding the above description. Although embodiments of the present invention have been described with reference to specific example embodiments, it will be recognized that the invention is not limited to the embodiments described, but can be practiced with modification and alteration within the spirit and scope of the appended claims. Accordingly, the specification and drawings are to be regarded in an illustrative sense rather than a restrictive sense. The scope of the invention should, therefore, be determined with reference to the appended claims, along with the full scope of equivalents to which such claims are entitled.

What is claimed is:
1. A system comprising:
a memory device; and
a processing device operatively coupled to the memory device, the processing device to:
determine a first midline of a dental arch that will exist after a treatment outcome for the dental arch;
receive image data of a face;

process the image data to determine a position of a second midline of the face;
generate a visual overlay comprising a virtual model of the dental arch that represents the treatment outcome for the dental arch, wherein the visual overlay comprises an indication of the second midline of the face and an indication of the first midline of the dental arch;
output the visual overlay to an augmented reality (AR) display or virtual reality (VR) display;
receive user input based on a user interaction with the virtual model of the dental arch, wherein the user input modifies the virtual model of the dental arch;
determine an update to the treatment outcome for the dental arch based on the user input;
generate an updated treatment plan based on the update to the treatment outcome; and
update the visual overlay, wherein the updated visual overlay comprises a view of the dental arch after the updated treatment outcome.

2. The system of claim 1, wherein
the image data of the face is received from an image capture device associated with the AR display.

3. The system of claim 1, wherein the user input comprises an update to the first midline of the treatment outcome, and wherein the processing device is further to update the first midline and the second midline based on the updated treatment plan.

4. The system of claim 1, wherein the virtual model is a virtual three-dimensional (3D) model, and wherein to receive the user input, the processing device is to:
receive additional image data from an image capture device associated with the AR display or the VR display;
identify an object in the image data; and
determine the update to the treatment outcome based on an interaction of the object with the virtual 3D model of the dental arch.

5. The system of claim 4, wherein to determine the update to the treatment outcome, the processing device is further to:
determine that the object is in a position corresponding to a virtual position of an element of the virtual 3D model;
determine a movement of the object relative to the element; and
generate an update to the treatment outcome comprising an update to the position of the element corresponding to the movement of the object relative to the element.

6. The system of claim 4, wherein the processing device is further to:
provide a first level of haptic feedback in response to the object interacting with the virtual 3D model of the dental arch; and
provide a second level of haptic feedback in response to a movement of an update to the treatment outcome satisfying a threshold.

7. The system of claim 2, wherein to output the visual overlay to the AR display or the VR display, the processing device is to:
detect a position of the dental arch in the image data; and
output the visual overlay to a position on the AR display to superimpose the visual overlay over a view of the dental arch on the AR display.

8. The system of claim 1, wherein the AR display comprises AR eyewear or AR headwear and wherein outputting the visual overlay to the AR display comprises projecting the visual overlay onto the AR eyewear or the AR headwear, and wherein the VR display comprises VR eyewear or VR headwear and wherein outputting the visual overlay to the VR display comprises projecting the visual overlay onto the VR eyewear or the VR headwear.

9. A system comprising:
a memory device; and
a processing device operatively coupled to the memory device, the processing device to:
generate a visual overlay comprising a virtual model of a dental arch that represents a treatment outcome for the dental arch;
output the visual overlay to an augmented reality (AR) display or virtual reality (VR) display;
receive user input based on a user interaction with the virtual model of the dental arch, wherein the user input modifies the virtual model of the dental arch;
determine an update to the treatment outcome for the dental arch based on the user input;
determine that the update to the treatment outcome violates a treatment outcome rule; and
output an indication that the treatment outcome violates the treatment outcome rule.

10. The system of claim 9, wherein:
the virtual model is a virtual three-dimensional (3D) model;
to receive the user input, the processing device is further to:
receive image data from an image capture device associated with the AR display or the VR display;
identify an object in the image data; and
determine the update to the treatment outcome based on an interaction of the object with the virtual 3D model of the dental arch; and
to output the indication that the treatment outcome violates the treatment outcome rule, the processing device is further to cause the object in the image data to provide haptic feedback.

11. A method comprising:
determining a first midline of a dental arch after a treatment outcome for the dental arch;
receiving image data of a face;
processing the image data to determine a position of a second midline of the face;
generating a visual overlay comprising a virtual model of the dental arch that represents the treatment outcome for the dental arch, wherein the visual overlay comprises an indication of the second midline of the face and an indication of the first midline of the dental arch;
outputting the visual overlay to an augmented reality (AR) display or virtual reality (VR) display;
receiving user input based on a user interaction with the virtual model of the dental arch, wherein the user input modifies the virtual model of the dental arch;
determining an update to the treatment outcome for the dental arch based on the user input;
generating an updated treatment plan based on the update to the treatment outcome; and
updating the visual overlay, wherein the updated visual overlay comprises a view of the dental arch after the updated treatment outcome.

12. The method of claim 11,
wherein the image data of the face is received from an image capture device associated with the AR display.

13. The method of claim 11, wherein the user input comprises an update to the first midline of the treatment outcome, the method further comprising:
updating the first midline and the second midline based on the updated treatment plan.

14. The method of claim 11, wherein the virtual model is a virtual three-dimensional (3D) model, the method further comprising:
  receiving additional image data from an image capture device associated with the AR display or the VR display;
  identifying an object in the image data; and
  determining the update to the treatment outcome based on an interaction of the object with the virtual 3D model of the dental arch.

15. The method of claim 14, wherein determining the update to the treatment outcome comprises:
  determining that the object is in a position corresponding to a virtual position of an element of the virtual 3D model;
  determining a movement of the object relative to the element; and
  generating an update to the treatment outcome comprising an update to the position of the element corresponding to the movement of the object relative to the element.

16. The method of claim 14, further comprising:
  providing a first level of haptic feedback in response to the object interacting with the virtual 3D model of the dental arch; and
  providing a second level of haptic feedback in response to a movement of an update to the treatment outcome satisfying a threshold.

17. The method of claim 12, wherein outputting the visual overlay to the AR display or the VR display comprises:
  detecting a position of the dental arch in the image data; and
  outputting the visual overlay to a position on the AR display to superimpose the visual overlay over a view of the dental arch on the AR display.

18. The method of claim 11, wherein the AR display comprises AR eyewear or AR headwear and wherein outputting the visual overlay to the AR display comprises projecting the visual overlay onto the AR eyewear or the AR headwear, and wherein the VR display comprises VR eyewear or VR headwear and wherein outputting the visual overlay to the VR display comprises projecting the visual overlay onto the VR eyewear or the VR headwear.

19. A method comprising:
  generating a visual overlay comprising a virtual model of a dental arch that represents a treatment outcome for the dental arch;
  outputting the visual overlay to an augmented reality (AR) display or virtual reality (VR) display;
  receiving user input based on a user interaction with the virtual model of the dental arch, wherein the user input modifies the virtual model of the dental arch;
  determining an update to the treatment outcome for the dental arch based on the user input;
  determining that the update to the treatment outcome violates a treatment outcome rule; and
  outputting an indication that the treatment outcome violates the treatment outcome rule.

20. The method of claim 19, wherein the virtual model is a virtual three-dimensional (3D) model, the method further comprising:
  receiving image data from an image capture device associated with the AR display or the VR display;
  identifying an object in the image data; and
  determining the update to the treatment outcome based on an interaction of the object with the virtual 3D model of the dental arch;
  wherein outputting the indication that the treatment outcome violates the treatment outcome rule comprises causing the object in the image data to provide haptic feedback to a user.

* * * * *